(12) United States Patent
Kopyov

(10) Patent No.: US 7,632,681 B2
(45) Date of Patent: Dec. 15, 2009

(54) COMPOSITIONS AND METHODS FOR PROPAGATION OF NEURAL PROGENITOR CELLS

(75) Inventor: Oleg V. Kopyov, Moorpark, CA (US)

(73) Assignee: Celavie Biosciences, LLC, Reading, PA (US)

( * ) Notice: Subject to any disclaimer, the term of this patent is extended or adjusted under 35 U.S.C. 154(b) by 136 days.

(21) Appl. No.: 11/002,933

(22) Filed: Dec. 2, 2004

(65) Prior Publication Data

US 2005/0118561 A1    Jun. 2, 2005

Related U.S. Application Data

(60) Provisional application No. 60/526,242, filed on Dec. 2, 2003.

(51) Int. Cl.
C12N 5/00 (2006.01)
C12N 5/02 (2006.01)
C12N 5/06 (2006.01)
C12N 5/08 (2006.01)

(52) U.S. Cl. .................. 435/404; 435/384; 435/377; 435/347; 435/368

(58) Field of Classification Search .......... 435/404, 435/384, 377, 347, 368
See application file for complete search history.

(56) References Cited

U.S. PATENT DOCUMENTS

| | | | |
|---|---|---|---|
| 5,750,376 A | 5/1998 | Weiss et al. | |
| 5,753,506 A | 5/1998 | Johe | |
| 5,843,780 A | 12/1998 | Thomson | |
| 5,851,832 A | 12/1998 | Weiss et al. | |
| 5,958,767 A * | 9/1999 | Snyder et al. | 435/368 |
| 5,968,829 A | 10/1999 | Carpenter | |
| 5,980,885 A | 11/1999 | Weiss et al. | |
| 5,981,165 A | 11/1999 | Weiss et al. | |
| 6,040,180 A | 3/2000 | Johe | |
| 6,071,889 A | 6/2000 | Weiss et al. | |
| 6,200,806 B1 | 3/2001 | Thomson | |
| 6,238,922 B1 | 5/2001 | Uchida | |
| 6,280,718 B1 | 8/2001 | Kaufman et al. | |
| 6,294,346 B1 | 9/2001 | Weiss et al. | |
| 6,399,369 B1 | 6/2002 | Weiss et al. | |
| 6,468,794 B1 | 10/2002 | Uchida et al. | |
| 6,497,872 B1 | 12/2002 | Weiss et al. | |
| 6,498,018 B1 | 12/2002 | Carpenter | |
| 6,602,711 B1 | 8/2003 | Thomson et al. | |
| 6,610,535 B1 * | 8/2003 | Lu et al. | 435/325 |
| 6,613,568 B2 | 9/2003 | Kaufman et al. | |
| 2001/0024825 A1 | 9/2001 | Thomson | |
| 2002/0178460 A1 * | 11/2002 | Enikolopov et al. | 800/18 |
| 2003/0008392 A1 | 1/2003 | Thomson | |
| 2003/0013193 A1 * | 1/2003 | Wu | 435/368 |
| 2003/0068819 A1 | 4/2003 | Zhang et al. | |
| 2003/0073234 A1 | 4/2003 | Amit et al. | |
| 2003/0166276 A1 | 9/2003 | Carpenter | |
| 2003/0190748 A1 | 10/2003 | Thomson | |
| 2004/0005701 A1 | 1/2004 | Xu et al. | |
| 2004/0023376 A1 | 2/2004 | Thomson et al. | |
| 2004/0224401 A1 | 11/2004 | Ludwig et al. | |

FOREIGN PATENT DOCUMENTS

WO    WO 94/10292    5/1994

OTHER PUBLICATIONS

Pluchino S, Zanotti L, Deleidi M, Martino G.2005. Neural stem cells and their use as therapeutic tool in neurological disorders. Brain Res Brain Res Rev. Apr.;48(2):211-9.*

Gerlach M, Braak H, Hartmann A, Jost WH, Odin P, Priller J, Schwarz J.2002. Current state of stem cell research for the treatment of Parkinson's disease. J Neurol. Oct.;249 Suppl 3:III/33-III-35.*

Wobus AM, Boheler KR.2005.Embryonic stem cells: prospects for developmental biology and cell therapy. Physiol Rev. Apr. ;85(2):635-78.*

Stanworth SJ, Newland AC. 2001. Stem cells: progress in research and edging towards the clinical setting .Clin Med. Sep.-Oct. ;1(5):378-82.*

Thomas CE, Ehrhardt A, Kay MA. 2003. Progress and problems with the use of viral vectors for gene therapy. Nat Rev Genet. May;4(5):346-58.*

Wolff JA, Fisher LJ, Xu L, Jinnah HA, Langlais PJ, Iuvone PM, O'Malley KL, Rosenberg MB, Shimohama S, Friedmann T, et al.Grafting fibroblasts genetically modified to produce L-dopa in a rat model of Parkinson disease.Proc Natl Acad Sci U S A. Nov. 1989;86(22):9011-4.*

Metz GA, Tse A, Ballermann M, Smith LK, Fouad K. The unilateral 6-0HDA rat model of Parkinson's disease revisited: an electromyographic and behavioural analysis. Eur J Neurosci. Aug. 2005;22(3):abstract.*

Eslamboli A.Marmoset monkey models of Parkinson's disease: which model, when and why? Brain Res Bull. Dec. 30, 2005;68(3):140-9. Epub Sep. 7, 2005.*

(Continued)

*Primary Examiner*—Valarie Bertoglio
(74) *Attorney, Agent, or Firm*—Karen S. Canady; canady + lortz LLP

(57) ABSTRACT

Compositions and methods for the culturing, propagation, cryopreservation and manipulation of neural progenitor cells (NPC) and pluripotent stem cells (PSC) are provided. The cells exhibit rapid doubling times and can be maintained in vitro for extended periods. Also provided is a method of propagating neural progenitor cells, and a method of transplanting human NPC and/or PSC to a host. The cells can be genetically modified to express a therapeutic agent prior to the transplanting.

29 Claims, 17 Drawing Sheets

OTHER PUBLICATIONS

Mandel RJ, Rendahl KG, Snyder RO, Leff SE. Progress in direct striatal delivery of L-dopa via gene therapy for treatment of Parkinson's disease using recombinant adeno-associated viral vectors.Exp Neurol. Sep. 1999;159(1):47-64. Review.*
Littlefield JW. Stepwise aggregation, compaction, and differentiation of uncompacted F9 cells. Dev Genet. 1989;10(5):402-10.*
Online Product search results for basic FGF, R & D Systems, printed Apr. 11, 2007. p. 1.*
Online Product search results for TGF alpha, R & D Systems, printed Apr. 11, 2007. p. 1.*
Online Product search results for EGF, R & D Systems, printed Apr. 11, 2007. p. 1.*
Online product literature for GIBCO Advanced D-MEM/F-12, printed Apr. 11, 2007, pp. 1-2.*
Keirstead HS.Stem cells for the treatment of myelin loss. Trends Neurosci. Dec. 2005;28(12):677-83. Epub Oct. 5, 2005.*
Yves Benniger et al., "Differentiation and Histological Analysis of Embryonic Stem Cell-derived Neural Transplants in Mice", *Brain Pathology*, 10: 330-341, 2001.
Christopher R. R. Bjornson et al., "Turning Brain into Blood: A Hematopoietic Fate Adopted by Adult Neural Stem Cells in Vivo", *Science*, 283: 534-537, Jan. 22, 1999.
M. K. Carpenter, "Enrichment of Neurons and Neural Precursors from Human Embryonic Stem Cells", *Exp Neurol*, 172(2):383-97, Dec. 2001, (1-Page Abstract Only).
Constance G. Craig et al., "In Vivo Growth Factor Expansion of Endogenous Subependymal Neural Precursor Cells Populations in the Adult Mouse Brain", *The Journal of Neuroscience*, 16(8):2649-2658, Apr. 15, 1996.
Rosemary A. Fricker et al., "Site-Specific Migration and Neuronal Differentiation of Human Neural Progenitor Cells after Transplantation in the Adult Rat Brain", *The Journal of Neuroscience*, 19(14):5990-6005, Jul. 15, 1999.
Nicholas Galano et al., "Transplantation as a Tool to Study Progenitors within the Vertebrate Nervous System", *J. Neurobiol.*, 36(2):152-61, Aug. 3, 1998.
Angela Gritti et al., "Multipotential Stem Cells from the Adult Mouse Brain Proliferate and Self-Renew in Response to Basic Fibroblast Growth Factor", *The Journal of Neuroscience*, 16(3):1091-1100, Feb. 1, 1996.
H. Georg Kuhn et al., "Neurogenesis in the Dentate Gyrus of the Adult Rat Age-Related Decrease of Neuronal Progenitor Proliferation", *The Journal of Neuroscience*, 16(6):2027-2033, Mar. 15, 1996.
H. Georg Kuhn et al., "Epidermal Growth Factor and Fibroblast Growth Factor-2 Have Different Effects on Neural Progenitors in the Adult Rat Brain", *The Journal of Neuroscience*, 17(15) 5820-5829, Aug. 1, 1997.
Randall D. Learish et al., "Rat Neurospheres Express mRNAs for TrkB, BDNF, NT-3 and p75", *Molecular Tools for Neuroscience*, Neural Notes Issue 19: 18-19, 2001.
Laura Lillen et al., "BMP and FGF Regulate the Development of EGF-responsive Neural Progenitor Cells", *Development*, 127: 4993-5005, (2000) printed in Great Britain © The Company of Biologists Limited 2000.
A. Martinez-Serrano et al., "Human Neural Stem and Progenitor Cells: in Vitro and in Vivo Properties, and Potential for Gene Therapy and Cell Replacement in the CNS", *Curr Gene Ther.*, 1(3):279-99, Sep. 2001, (1-Page Abstract Only).
Eva Mezey et al., "Turning Blood into Brain: Cells Bearing Neuronal Antigens Generated in Vivo from Bone Marrow", *Science*, 290: 1779-1782, Dec. 1, 2000.
Lars Olson, "Grafts and Growth Factors in CNS", *Proceedings of the Xth Meeting of the World Society for Sterotactic and Functional Neurosurgery*, Maebashi, Japan, Oct. 1989, Stereotact Funct Neurosurg 1990;54+55:250-267.
Kook In Park et al., "Transplantation of Neural Progenitor and Stem Cells: Developmental Insights May Suggest New Therapies for Spinal Cord and Other CNS Dysfunction", *Journal of Neurotrauma*, 16(8), 1999.
Benjamin E. Reubinoff et al., "Embryonic Stem Cell Lines from Human Blastocysts: Somatic Differentiation in Vitro", *Nature Biotechnology*, 18: 399-404, Apr. 2000.
Clive N. Svendsen et al, "Long-Term Survival of Human Central Nervous System Progenitor Cells Transplanted into a Rat Model of Parkinson's Disease", *Experimental Neurology*, 148: 135-146, 1997.
Clive N. Svendsen et al., "A New Method for the Rapid and Long Term Growth of Human Neural Precursor Cells", *Journal of Neuroscience Methods*, 85: 141-152, 1998.
James A. Thomson et al., "Embryonic Stem Cell Lines Derived from Human Blastocysts", *Science*, 282: 1145-1147, Nov. 6, 1998.
Vincent Tropepe et al., "Distinct Neural Stem Cells Proliferate in Response to EGF and FGF in the Developing Mouse Telencephalon", *Developmental Biology*, 208: 166-188, 1999.
Christian Winkler et al., "Incorporation and Glial Differentiation of Mouse EGF-Responsive Neural Progenitor Cells after Transplantation into the Embryonic Rat Brain", *Molecular and Cellular Neuroscience*, 11: 99-116, 1998.
Feng C. Zhou et al., "Long-term Nonpassaged EGF-responsive Neural Precursor Cells are Stem Cells", *Wound Repair and Regeneration*, 6(4):S-337-S-348, 1998.
F. C. Zhou et al., "Three to Four-year-old Nonpassaged EGF-responsive Neural Progenitor Cells: Proliferation, Apoptosis, and DNA Repair", *Exp Neurol*, 164(1):200-8, 2000, (1-Page Abstract Only).
van Leeuwen, J. et al., "Role of extracellular calcium in the regulation of 1,25-dihydroxyvitamin D3 formation in . . . ," Biochimica et Biophysica Acta 1221:167-170 (1994).
USPTO Office Action mailed on Apr. 20, 2009 in the related Continuation-in-Part U.S. Appl. No. 11/755,224 filed on May 30, 2007, Inventor: Oleg V. Kopyov (c+I CBL.2-US-I1) 13 pp.

* cited by examiner

Fig. 14. BrDU-positive cells in M5 line suspension. DAB staining. 40x

Fig. 15. Showing BrDU-Positive M3 single cell suspension. Fluorescein-labled, 20x Fig. 16. Nestin-positive single cell suspension (M3). Fluorescein-labeled 20x.

COMPOSITIONS AND METHODS FOR PROPAGATION OF NEURAL PROGENITOR CELLS

This application claims the benefit of U.S. provisional patent application No. 60/526,242, filed Dec. 2, 2003, the entire contents of which are incorporated herein by reference. Throughout this application various publications are referenced. The disclosures of these publications in their entireties are hereby incorporated by reference into this application in order to describe more fully the state of the art to which this invention pertains.

TECHNICAL FIELD OF THE INVENTION

The present invention relates generally to propagation and use of pluripotent stem cells and neural progenitor cells. The invention provides compositions and methods for isolation, preparation, growth, cryopreservation, differentiation and transplantation of stem and neural progenitor cells. The stem cells and neural progenitor cells can be useful for therapeutic, diagnostic and research purposes.

BACKGROUND OF THE INVENTION

Disorders of the central nervous system (CNS) include a number and variety of conditions, such as neurodegenerative diseases (e.g. Alzheimer's and Parkinson's), acute brain injury (e.g. stroke, head trauma, cerebral palsy) and neurological dysfunction (e.g. depression, epilepsy, schizophrenia). As the elderly population grows, neurodegenerative disease becomes an increasingly important concern, as the risk for many of these disorders increases with age. These neurodegenerative diseases, which include Alzheimer's disease (AD), multiple sclerosis (MS), Huntington's disease (HD), amyotrophic lateral sclerosis (ALS), and Parkinson's disease (PD), have been linked to the degeneration of neural cells in identified locations of the CNS, resulting in an inability of these cells or the relevant brain region to carry out their intended function.

Treatment for CNS disorders via the administration of pharmaceutical compounds has drawbacks, including the limited range of drugs capable of crossing the blood-brain barrier and the drug-tolerance that develops in patients receiving long-term treatment. For example, Parkinson's patients treated with levodopa (L-dopa), a dopamine precursor that is able to cross the blood-brain barrier become tolerant to the effects of L-dopa, and steadily increasing dosages are needed to maintain its effects. In addition, there are a number of side effects associated with L-dopa, such as increased and uncontrollable movement.

Over 1.5 million people in the United States suffer from Parkinson's disease (PD). Once pharmacological treatment for PD is exhausted, patient can only turn to surgical interventions. Current interventions focus on containing PD symptoms, but it is imperative to attempt to reverse the damage of the disease. Such restoration may be possible through transplantation of neural progenitor cells.

Grafting of fetal neural tissue has been applied to the treatment of neurological diseases such as Parkinson's disease. Fetal neural grafts may avert the need for constant drug administration, and also for drug delivery systems designed to circumvent the blood-brain barrier. However, the cells used for transplantation can induce an immune reaction in the host recipient. In addition, the cells must be at a stage of development where they are able to form normal neural connections with neighboring cells.

Grafting also offers a therapeutic approach to demyelinating diseases, such as multiple sclerosis (MS). In both human demyelinating diseases and rodent models there is substantial evidence that demyelinated neurons are capable of remyelination in vivo. In MS, for example, it appears that there are often cycles of de- and remyelination. Exogenously applied cells have been shown to be capable of remyelinating demyelinated axons in a number of experimental conditions (See Freidman et al., Brain Research, 378:142-146, 1986; Raine, et al., Laboratory Investigation 59:467-476, 1988). Success has been shown using dissociated glial cell suspensions prepared from spinal cords Duncan et al., J. Neurocytology, 17:351-360 (1988); Schwann cell cultures prepared from sciatic nerve (Bunge et al., 1992, WO 92/03536; Blakemore and Crang, J. Neurol. Sci., 70:207-223, 1985); cultures from dissociated brain tissue (Blakemore and Crang, Dev. Neurosci. 10:1-11, 1988); oligodendrocyte precursor cells (Gumpel et al., Dev. Neurosci. 11:132-139, 1989); O-2A cells (Wolswijk et al., Development 109:691-608, 1990; Raff et al., Nature 3030:390-396, 1983; Hardy et al., Development 111:1061-1080, 1991); and immortalized O-2A cell lines (Almazan and McKay, Brain Res. 579:234-245, 1992).

O-2A cells are glial progenitor cells which give rise in vitro only to oligodendrocytes and type II astrocytes. Cells immunopositive in vivo for the O-2A phenotype have been shown to successfully remyelinate demyelinated neurons in vivo, (Godfraind et al., J. Cell Biol. 109:2405-2416, 1989). Injection of a large number of O-2A cells is required to adequately remyelinate all targeted neurons in vivo. Although O-2A progenitor cells can be grown in culture, they are capable of only a limited number of divisions (Raff Science 243:1450-1455, 1989). In addition, the isolation technique employs a low yield source (optic nerve) and requires a number of purification steps.

Various approaches to neurotransplantation have been developed to ameliorate neurological disease, including the grafting of neurons from the adult PNS to produce dopamine (Notter, et al., Cell Tissue Research 244:69-76, 1986), transplantation of monoamine-containing cells isolated from adult rat pineal gland and adrenal medulla into rat frontal cortex to alleviate learned helplessness, a form of depression (U.S. Pat. No. 4,980,174); grafting of chromaffin cells and adrenal medullary into the brain stem or spinal cord of rats to produce analgesia when the implanted tissue or cell was induced to release catecholamines (U.S. Pat. No. 4,753,635). Adrenal cells, however, do not obtain a normal neural phenotype upon grafting into the CNS, and are therefore of limited use for transplants where synaptic connections must be formed.

Another approach to neurotransplantation involves the use of genetically modified cells. Using this method, a foreign gene or transgene is introduced into a cell to allow the cell to express the gene. Cells modified to contain the transferred gene can be transplanted to the site of neurodegeneration, and provide products such as neurotransmitters and growth factors (Rosenberg, et al., Science 242:1575-1578, 1988) which may function to alleviate some of the symptoms of degeneration. Genetically modified cells have been used in neurological tissue grafting in order to replace lost cells. For example, fibroblasts have been genetically modified with a retroviral vector containing a cDNA for tyrosine hydroxylase, which allows them to produce dopamine, and implanted into animal models of Parkinson's Disease (U.S. Pat. No. 5,082,670). However, there remains a risk of inducing an immune reaction using currently available cell lines, and these cells may not achieve normal neuronal connections within the host tissue.

While attempts have been made to propagate neural progenitor cells for use in neurotransplantation and for drug screening, these efforts have met with limited success. Neurobasal medium has allowed for fast doubling times of cultured neural progenitor cells, but these doubling times are observed for about one month, after which the cells differentiate and lose their progenitor phenotype. Typically, with the most optimal culture conditions, neural progenitor cells will survive for only about 10 passages in culture. In addition, only about 1-2% of neural progenitor cells survive cryopreservation. Moreover, current efforts to maintain neural progenitor cells in vitro require the use of a feeder layer and/or introduce animal components. Even with use of a feeder layer, neural progenitor cells have been maintained for only about 6 months. For clinical applications, it is desirable to obtain and maintain human neural progenitor cells that are free of animal components and do not require the use of a feeder layer.

There remains a need for a large quantities of undifferentiated neural progenitor cells and pluripotent stem cells for transplantation and for drug screening, particularly for human progenitor and stem cells. A need also exists for neural progenitor cells that are capable of long-term proliferation in vitro and that are amenable to controlled differentiation and/or genetic modification. In particular, there is a need for methods of maintaining and propagating neural progenitor cells for extended periods of time, and for methods that optimize yield following cryopreservation.

SUMMARY OF THE INVENTION

The invention provides compositions and methods for the culturing, propagation, cryopreservation, and manipulation of neural progenitor cells (NPC) and pluripotent stem cells. The invention provides a culture medium, wherein the calcium concentration of the medium is not greater than 0.15 mM, and in some embodiments, not greater than about 0.06 mM. In some embodiments, the calcium concentration of the medium is from about 0.05 mM-0.15 mM. The culture medium further comprises about 20 ng/ml (optionally, from about 20 to about 100 ng/ml) epidermal growth factor (EGF), about 10 ng/ml (optionally, from about 10 to about 50 ng/ml) basic fibroblast growth factor (bFGF), and about 10 ng/ml (optionally, from about 10 to about 150 ng/ml) transforming growth factor-alpha (TGFα), and, optionally, about 7 to about 30 ng/ml leukemia inhibiting factor (LIF). Also provided is a cell culture comprising NPC suspended in the medium. The cell culture is successfully maintained in the absence of a feeder layer, and in the absence of products derived from non-human animal sources.

In one embodiment, the cell culture further comprises about 0.03 to about 0.09 mM calcium chloride, wherein the medium is brought to full volume in a calcium-free minimum essential medium and has a total calcium concentration of less than 0.1 mM. In another embodiment, the total calcium concentration is about 0.05-0.06 mM. For cryopreservation, the low calcium medium is supplemented with B27 (typically about 2%) and dimethyl sulfoxide (typically about DMSO) (10%), and the trophic factors used in the expansion culture medium. NPC cryopreserved in accordance with the invention exhibit a viability rate of greater than 50%. In one embodiment, the viability rate following freeze-thaw is greater than 75%. Post-cryopreservation viability of over 90% has been observed, with greater than 95% viability being typical of NPC cryopreserved with the medium of the invention.

Preferably, the culture medium is serum-free and free of non-human animal products. The medium can further comprise 2% B27 supplement. Typically, the growth factors, EGF, bFGF, LIF and TGFα, are recombinant growth factors, and the NPC and the growth factors are human.

In one embodiment, the NPC are derived from fetal forebrain. The NPC cultured in accordance with the invention have a doubling rate of less than 12 days, typically about 5 days. The NPC can continue to proliferate for at least 1 year in vitro. NPC of the invention have been observed to continue proliferating for over 2.5 years and after over 250 passages.

The invention further provides a method of propagating neural progenitor cells, comprising culturing primary human fetal brain tissue in a culture medium of the invention. The invention additionally provides a method of cryopreserving NPC and of optimizing NPC survival upon thawing. Also provided is a method of transplanting human NPC to a host. In one embodiment, L-glutamine and leukemia inhibitory factor (LIF) are added to the culture medium prior to the transplanting to promote neuronal growth over glia. In another embodiment, the cell culture is transplanted to multiple sites within the host. In yet a further embodiment, the NPC are genetically modified to express a therapeutic agent prior to the transplanting.

The invention additionally provides a method of propagating pluripotent stem cells (PSC). The method comprises culturing primary human fetal forebrain tissue in a culture medium of the invention. The cultures can be monitored for the expression of Oct4, a stem cell marker whose expression has been shown to increase in prevalence among cells cultured by the method of the invention over a period of months.

DETAILED DESCRIPTION OF THE INVENTION

Figure 1:
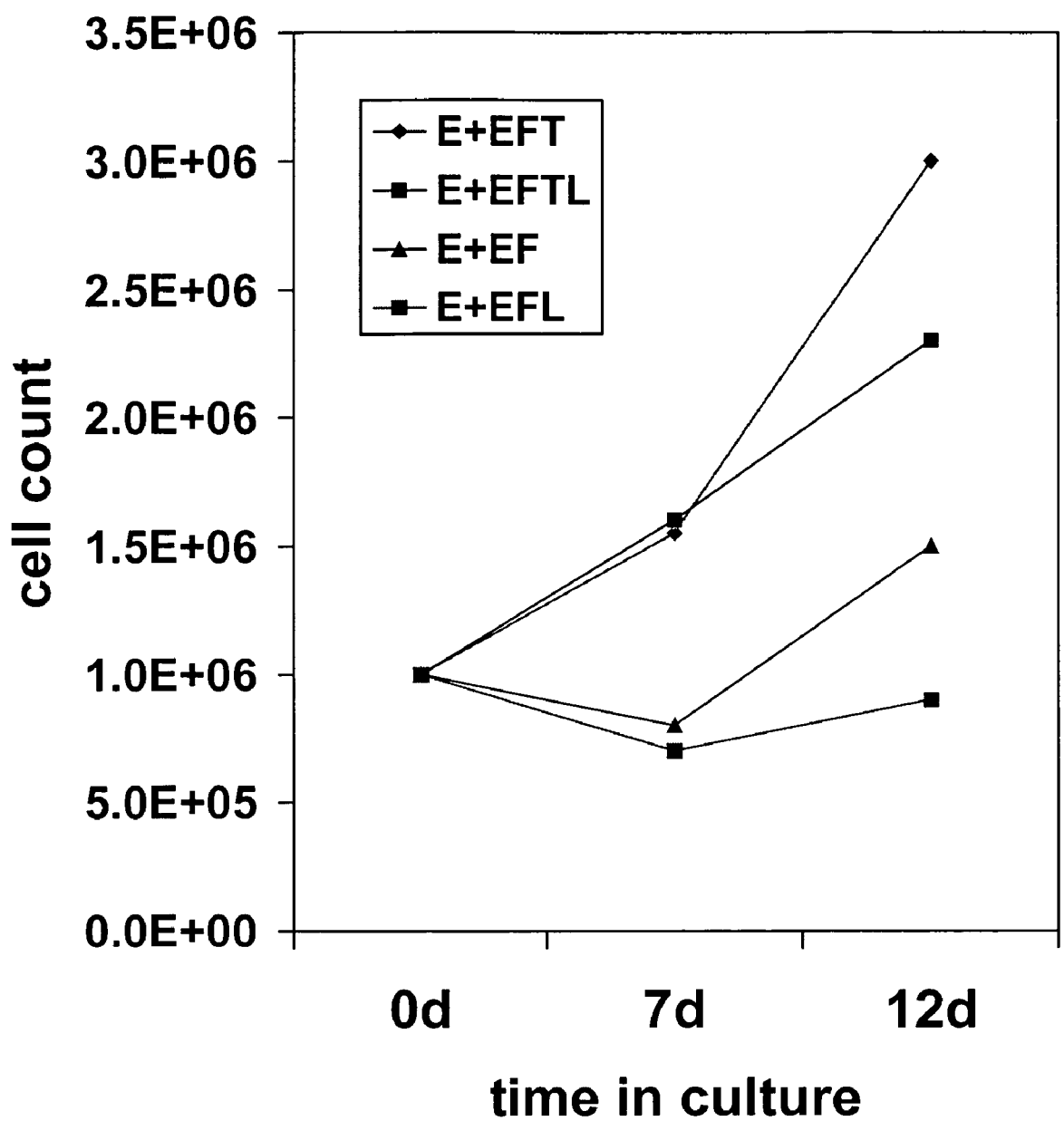
FIG. 1 is a graph showing the growth of cultured NPC in low calcium (0.06 mM) EMEM supplemented with ("E+") various combinations of EGF (E), bFGF (F), TGFα (T) and LIF (L). E+EFT provided optimal growth of NPC in suspension.
Figure 2:
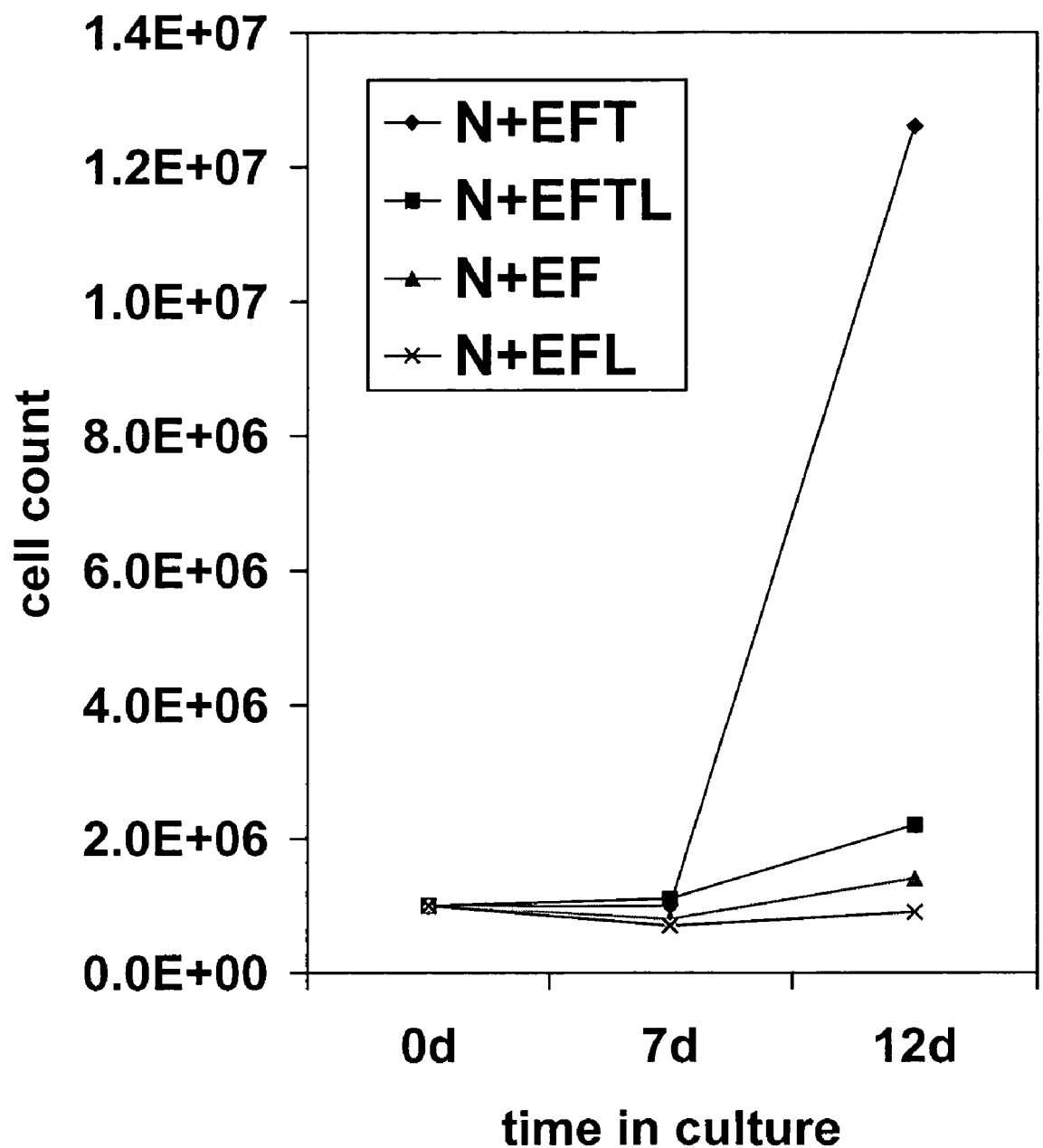
FIG. 2 is a graph showing the growth of cultured NPC in Neurobasal™ medium supplemented with (N+) various combinations of EGF (E), bFGF (F), TGFα (T) and LIF (L). N+EFT provided optimal growth of attached cells. Growth rates declined, however, after 3-4 months in vitro.
Figure 3:
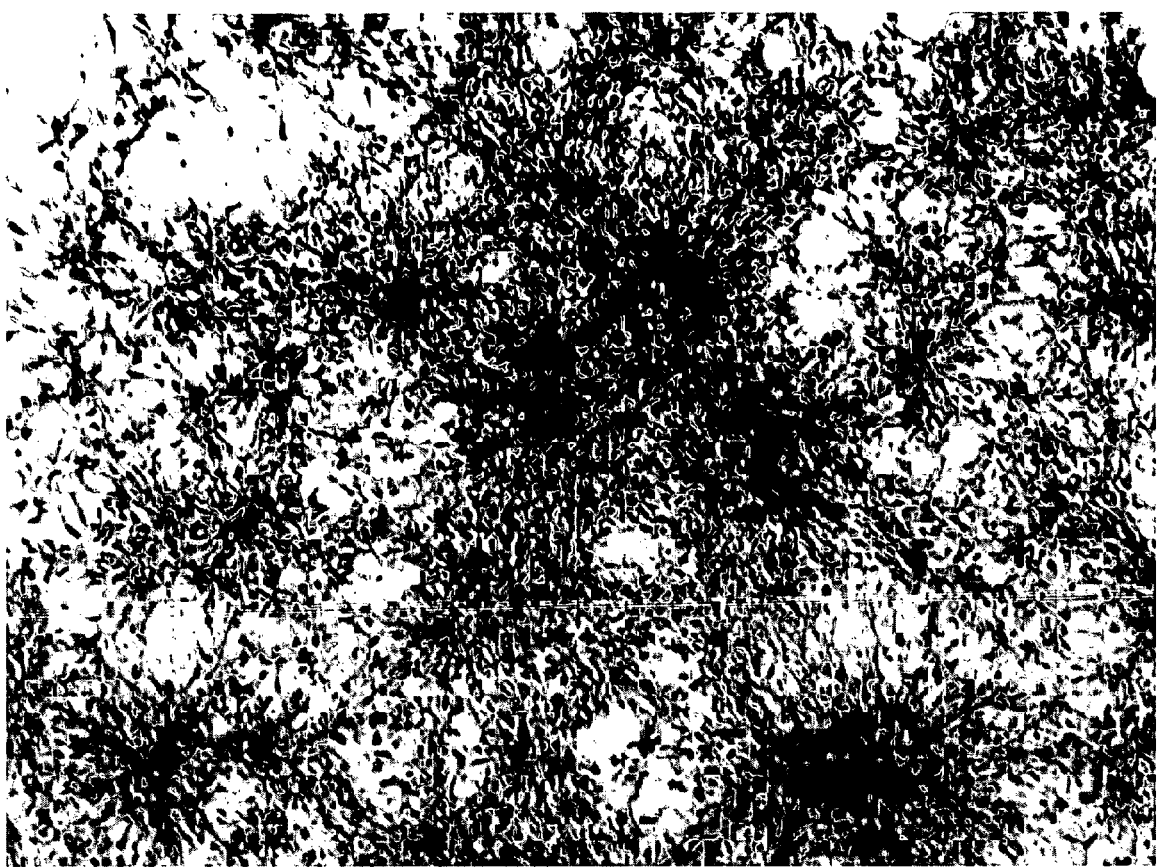
FIG. 3 is a photomicrograph showing immunohistochemistry of T and M brain progenitor lines. A strong BrDU-positive reaction was observed in the M5 line cells after 138 passages. 20× magnification.

The present invention is based on the discovery of a culture medium optimized for long-term growth of human neural progenitor cells (NPC), and for successful cryopreservation of NPC. NPC cultured in accordance with the invention are capable of surviving in vitro for longer than one year, and as long as three years. Cryopreservation of NPC in accordance with the invention results in over 95% viability upon thawing. In addition, the invention provides variations on the culture medium that allow for manipulation of the cultured NPC to achieve attachment and differentiation when desired. NPC cultured in accordance with the invention have been successfully transplanted into the brain, providing restoration of structure and function in an animal model of Parkinson's disease. Moreover, the same culture conditions used to propagate NPC have also been shown to cultivate pluripotent stem cells (PSC) that express the stem cell marker, Oct4.

Definitions

All scientific and technical terms used in this application have meanings commonly used in the art unless otherwise specified. As used in this application, the following words or phrases have the meanings specified.

As used herein, "low calcium" medium refers to less than 0.15 mM calcium (final concentration), and typically about 0.03-0.09 mM. Low calcium medium does not include calcium-free medium. "High calcium" medium refers to greater than 0.15 mM calcium.

As used herein, "neural progenitor cell" (NPC) refers to cells that are immunopositive for nestin, capable of continuous growth in suspension cultures and, upon exposure to appropriate conditions, can differentiate into neurons or glial cells. A neural progenitor cell, as referred to herein, is capable of surviving for at least 2-3 years in vitro.

As used herein, "pluripotent stem cell" (PSC) refers to cells that are immunopositive for the stem cell marker, Oct4.

As used herein, "genetically modified" refers to cells that have been manipulated to contain a transgene by natural or recombinant methods. For example, NPC or their progeny can be genetically modified by introducing a nucleic acid molecule that encodes a desired polypeptide.

As used herein, "transgene" means DNA that is inserted into a cell and that encodes an amino acid sequence corresponding to a functional protein. Typically, the encoded protein is capable of exerting a therapeutic or regulatory effect on cells of the CNS.

As used herein, "protein" or "polypeptide" includes proteins, functional fragments of proteins, and peptides, whether isolated from natural sources, produced by recombinant techniques or chemically synthesized. Polypeptides of the invention typically comprise at least about 6 amino acids, and are sufficiently long to exert a biological or therapeutic effect.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

The term "nucleic acid" or "polynucleotide" refers to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline.

Compositions comprising such carriers are formulated by well known conventional methods (see, for example, *Remington's Pharmaceutical Sciences,* 18th edition, A. Gennaro, ed., Mack Publishing Co., Easton, Pa., 1990).

As used herein, "a" or "an" means at least one, unless clearly indicated otherwise.

Neural Progenitor Cells

The invention provides neural progenitor cells (NPC) that can be maintained indefinitely in culture, stain positively for bromodeoxyuridine (BrdU) and nestin, and are multipotent. The NPC of the invention are capable of generating neurons (e.g., MAP2, neuron specific enolase or neurofilament positive cells) and glia (e.g., GFAP or galactocerebroside positive cells). NPC of the invention can be maintained in cell culture, typically as a suspension culture, for at least one year. The NPC described herein have been maintained for as long as 2.5 years, with some NPC having been cultured for three years.

The NPC of the invention exhibit 50% growth in the first 2 days in culture, and doubling times of less than 10 days, typically about 6 days. Doubling times of as little as 5 days have been observed. In addition, these cells continue to grow in culture for extended periods of time. Unlike NPC cultured in conventional media such as Neurobasal™ medium, however, these cultures do not show a decline after 3-4 months, but continue to survive and expand for years, and through hundreds of passages.

Figure 4:
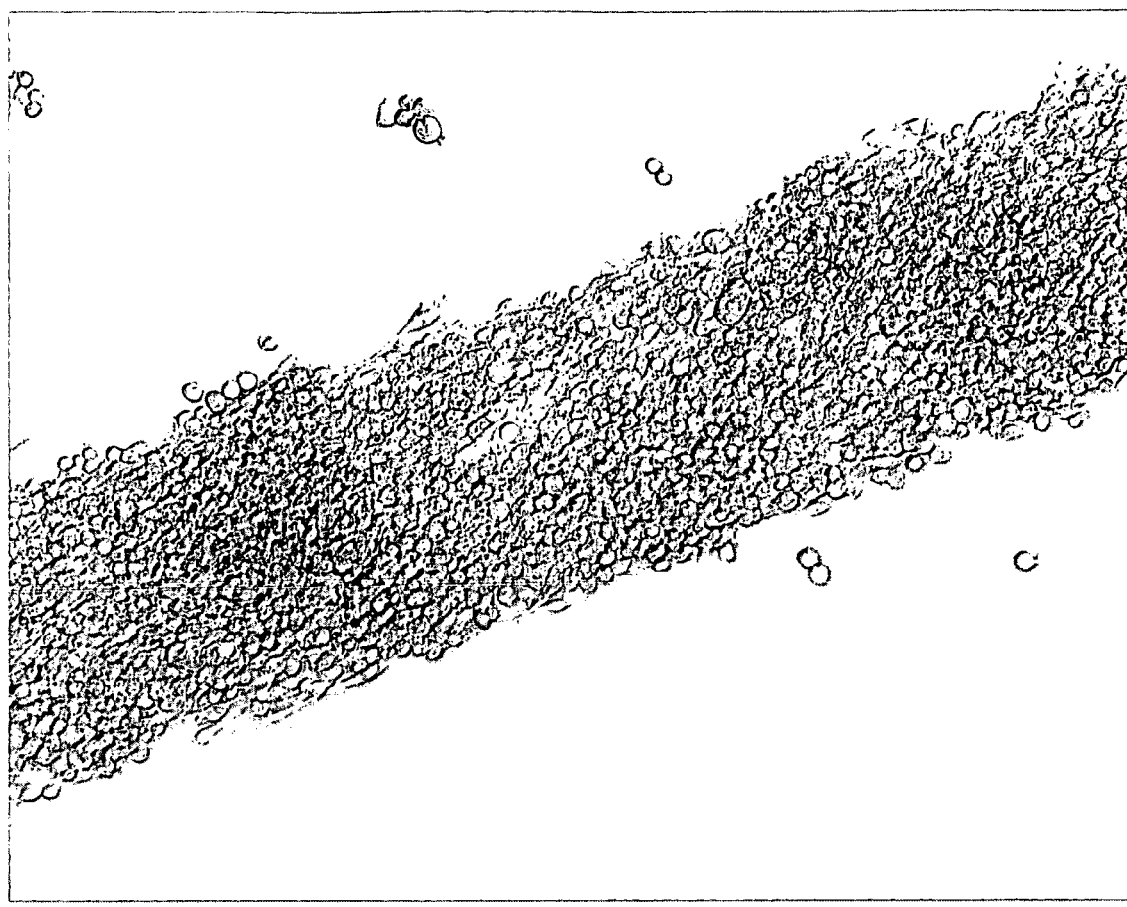
FIG. 4 is a phase contrast photomicrograph that shows a confluent growth of M5 NPC cells. Almost all cells maintain undifferentiated condition. 10× magnification.
Figure 5:
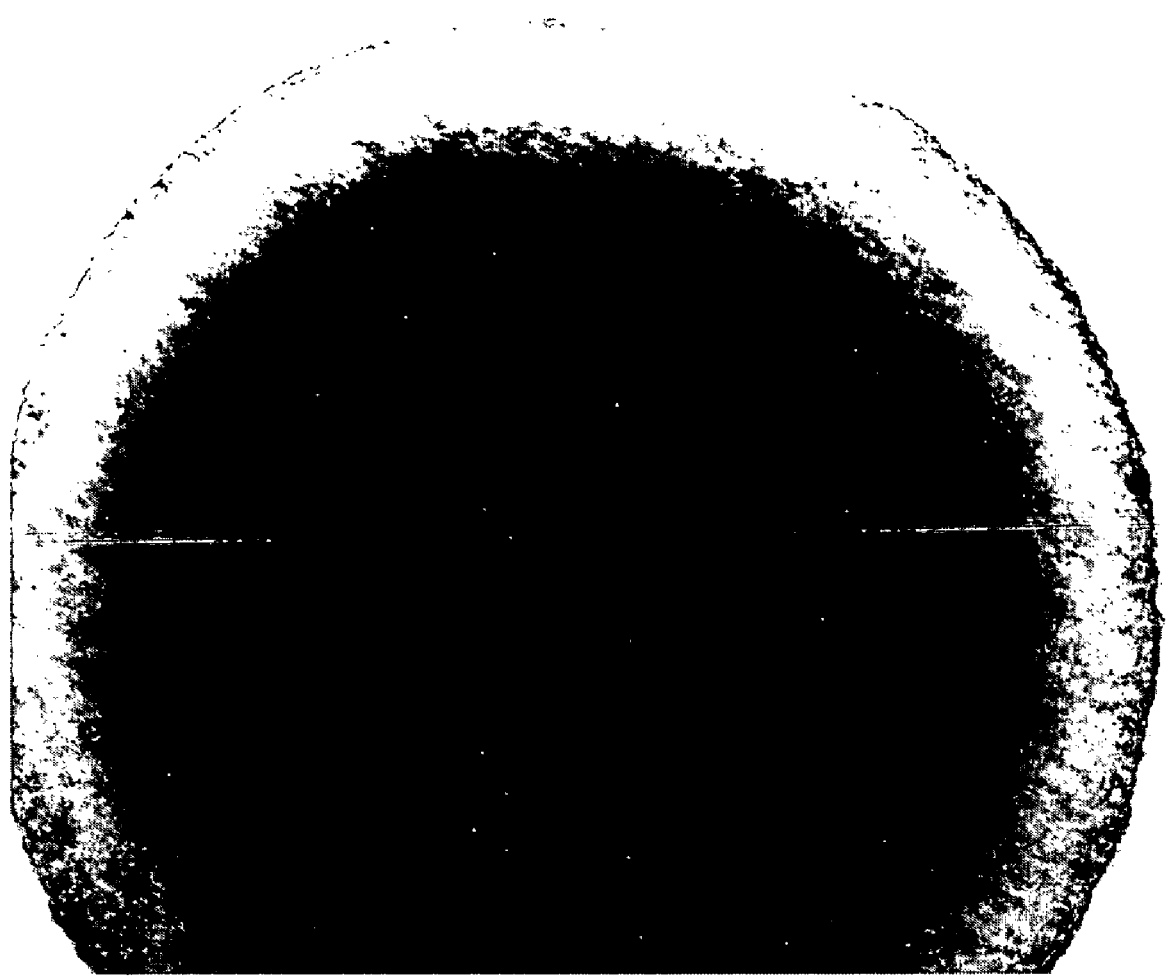
FIG. 5 is a phase contrast photomicrograph that shows a typical "embryoid body" formed by the brain progenitor cells and characteristic for stem/progenitor cells. 10× magnification.
Figure 6:
FIG. 6 is a phase contrast photomicrograph that shows brain progenitor cells from the $5^{th}$ passage of T5 line growing in small floating clusters. 10× magnification.
Figure 12:
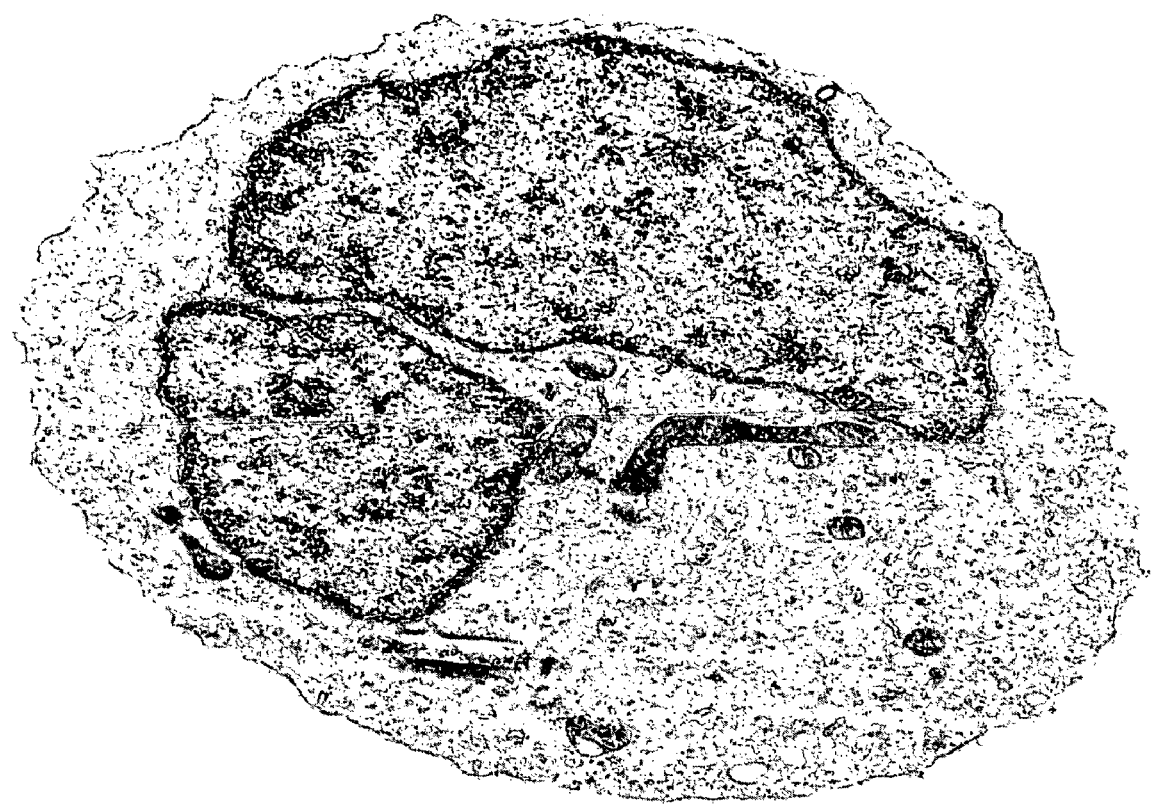
FIG. 12 is an electron micrograph showing the ultrastructure of an undifferentiated NPC from T5 line. 13,000× magnification.
Figure 13:
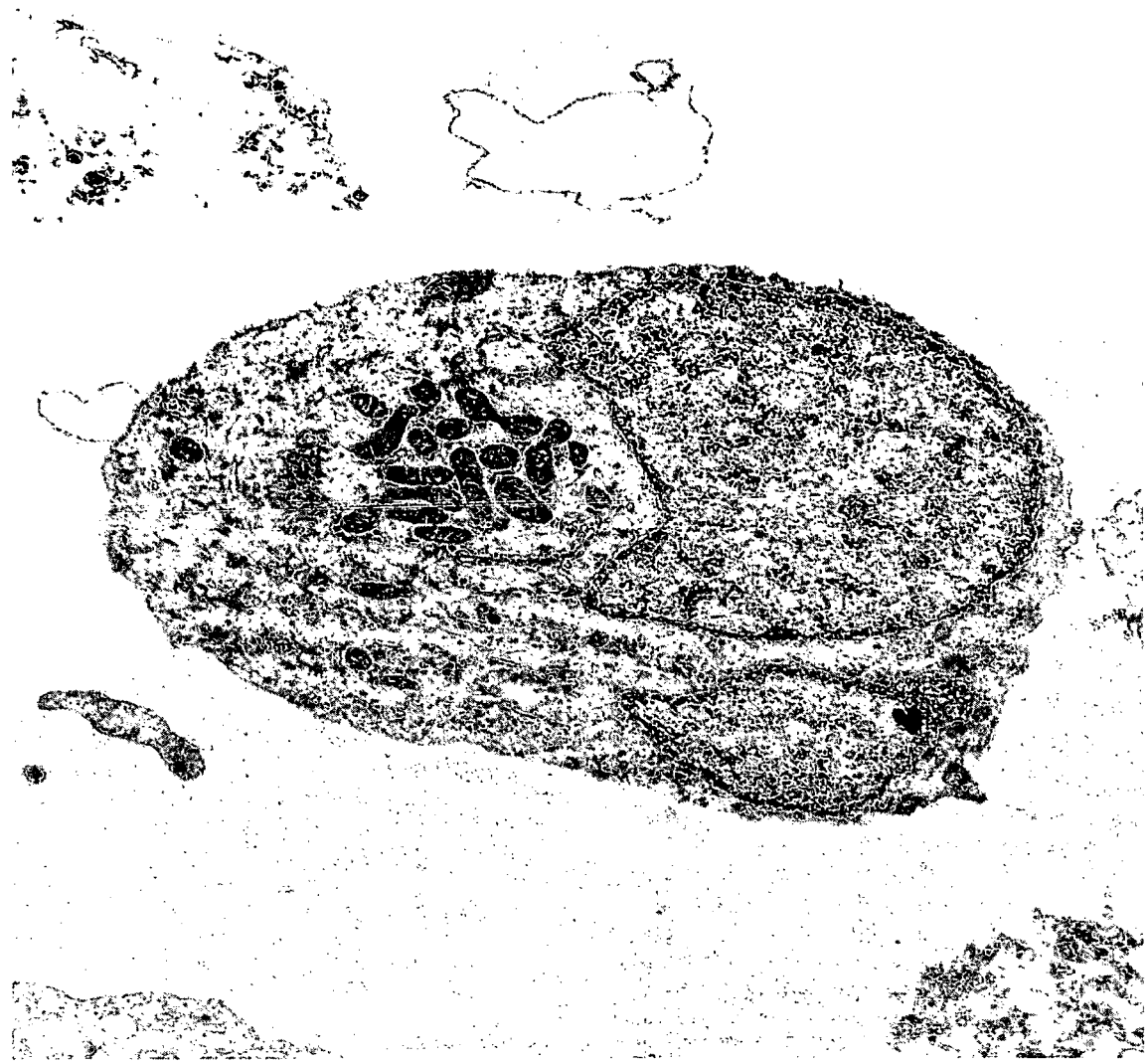
FIG. 13 is an electron micrograph showing the ultrastructure of a NPC from M5 line. Its cytoplasm contains many mitochondria. 13,000× magnification.
Figure 14:
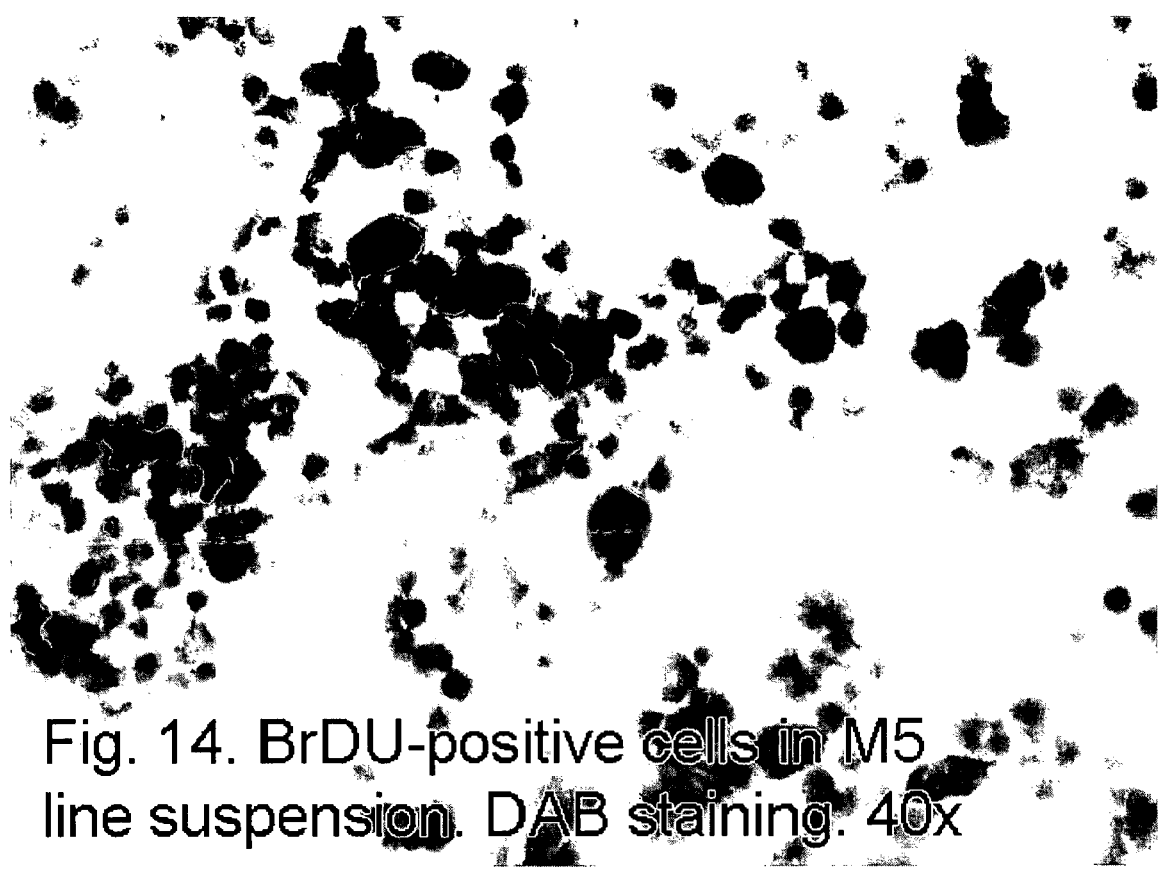
FIG. 14 is a photomicrograph showing bromodeoxyuridine (BrDU) immunopositive NPC in a M5 line suspension. Immunoreactive cells stained with diaminobenzidine (DAB). 40× magnification.
Figure 15:
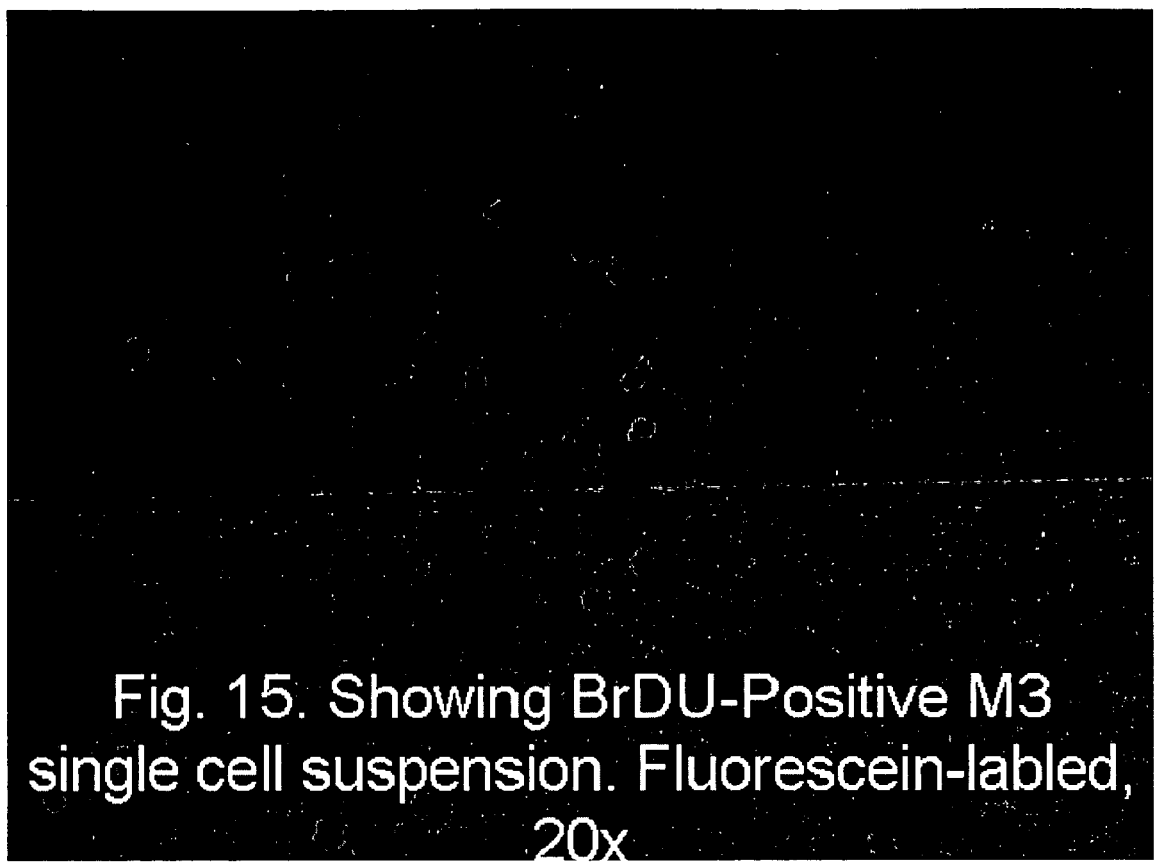
FIG. 15 is a photomicrograph showing bromodeoxyuridine (BrDU) immunopositive NPC in a M3 single cell suspension. Immunoreactive cells labeled with fluorescein. 20× magnification.
Figure 16:
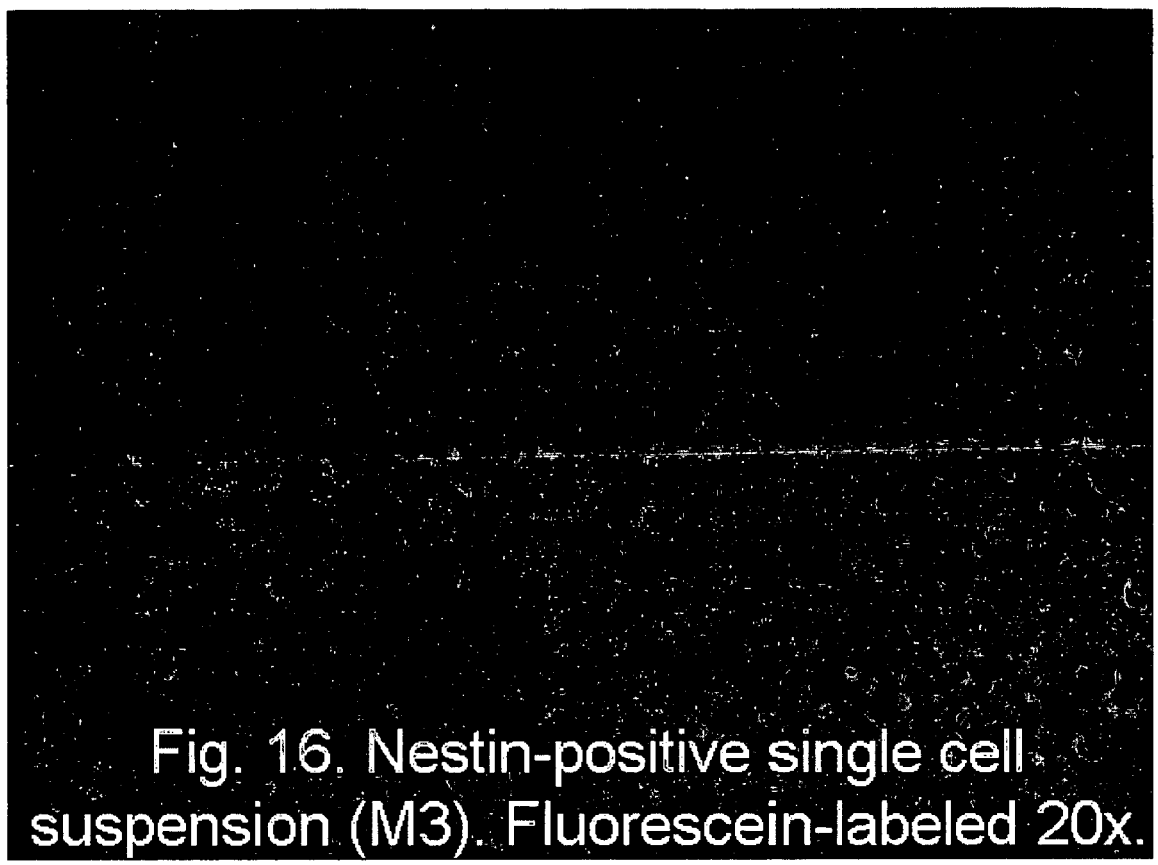
FIG. 16 is a photomicrograph showing nestin immunopositive NPC in a M3 single cell suspension. Immunoreactive cells labeled with fluorescein. 20× magnification.

In addition, the NPC of the invention exhibit normal structure and function that is typical of progenitor cells. As shown in FIG. 5, NPC form embryoid bodies in culture. FIG. 4 shows a confluent growth of NPC that remain undifferentiated, and FIG. 6 shows NPC growing in floating clusters. FIGS. 12 and 13 are electron micrographs, showing the normal ultrastructure of NPC of the invention.

NPC can be prepared from mesencephalon and/or telencephalon of fetal brain, as described in Example 1 below. Typically, the tissue is dissected in a general purpose serum-free medium, such as Hank's Balanced Salt Solution (HBSS) with 0.25 ug/ml of Fungizone and 10 ug/ml of Gentamicin, under sterile conditions.

Pluripotent Stem Cells

The invention provides pluripotent stem cells (PSC) that can be maintained indefinitely in culture, and that stain positively for the stem cell marker Oct4. The PSC of the invention co-express Oct4 and nestin, indicating that these cells are capable of generating neurons and glia. PSC of the invention can be maintained in cell culture, typically as a suspension culture, for at least one year. The progenitor/stem cell cultures described herein will initially include a small percentage of Oct4-positive cells, and mostly nestin-positive NPC cells. Over a period of months in culture, the proportion of Oct4-positive cells increases significantly. For example, a typical culture will shift from being 5% Oct4-positive cells to up to 30% Oct4-positive cells in four months.

The PSC of the invention can be used in all the ways described herein for NPC. The Oct4-positive status of these cells indicates that they are capable of many additional uses beyond the neural environment. The pluripotent nature of these cells make them attractive for placement in a variety of tissue environments, wherein local cytokines (natural and/or exogenously supplied) and other signals induce appropriate differentiation and migration. In the description of methods that follows, it is understood that NPC refers to NPC and/or PSC.

Media and Methods for Cell Culture

Figure 7:
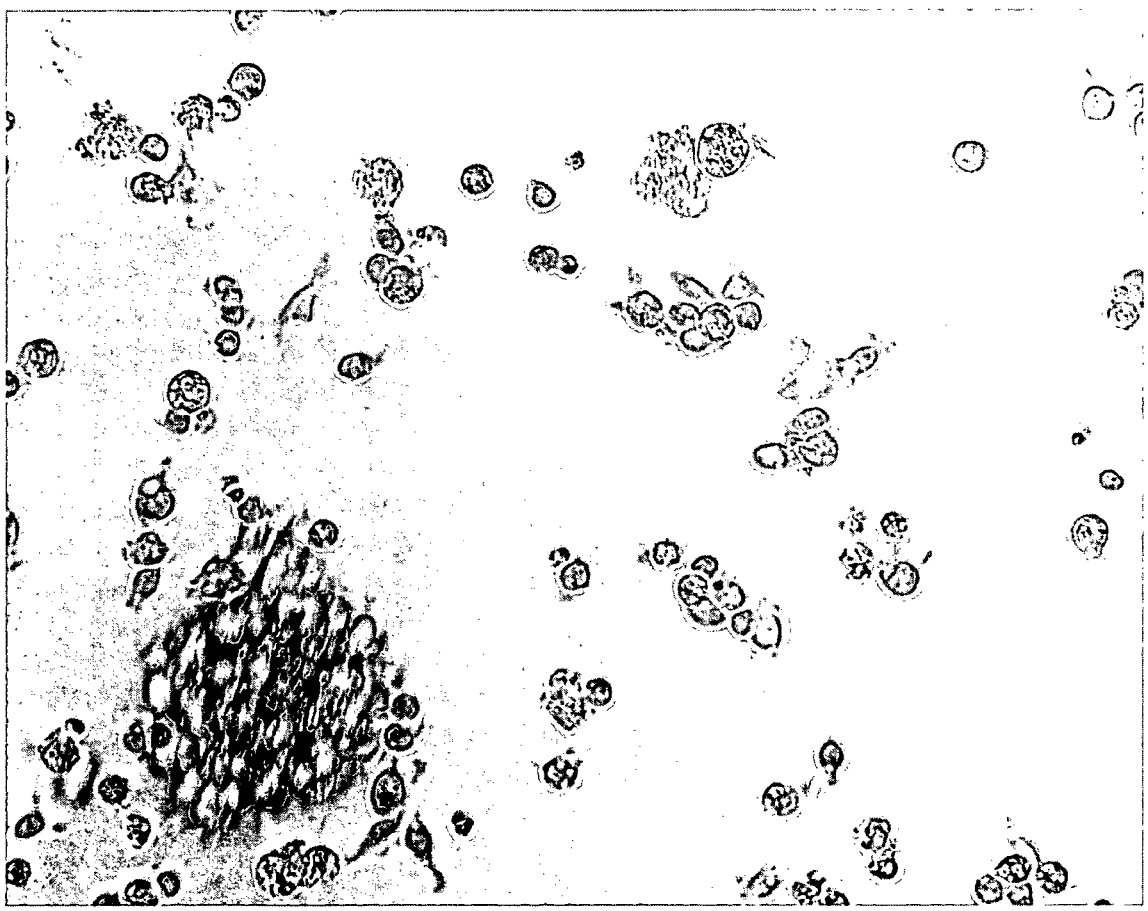
FIG. 7 is a phase contrast photomicrograph that shows a small floating cluster of the NPC and a number of the NPC cells that are getting attached to the culture flask due to the increase in medium $Ca^{++}$ concentration from 0.05 mMol to 0.1 mMol. 10× magnification.
Figure 8:
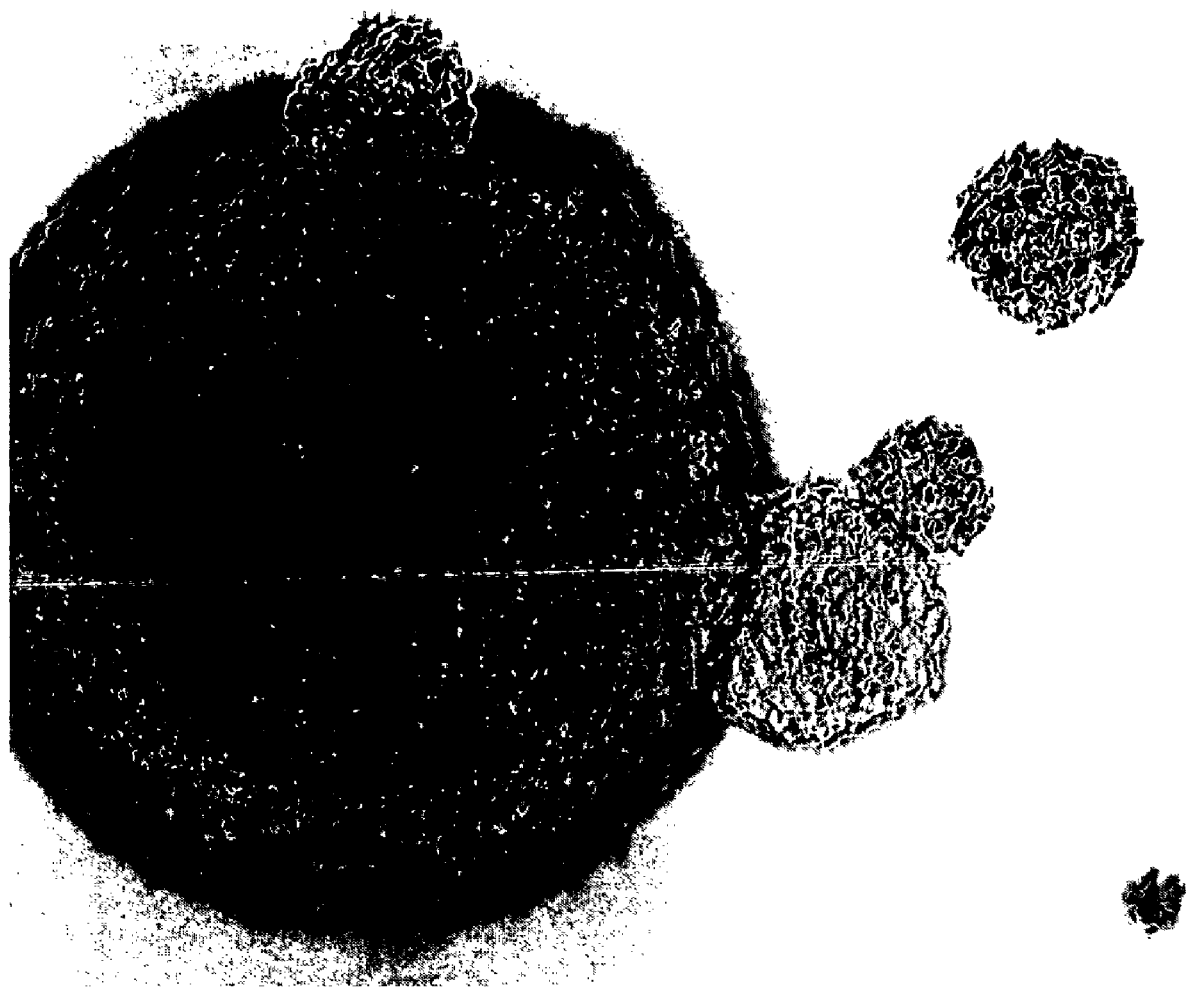
FIG. 8 is a phase contrast photomicrograph that shows the NPC from T5 line growing as embryoid bodies. $154^{th}$ passage. 10× magnification.
Figure 9:
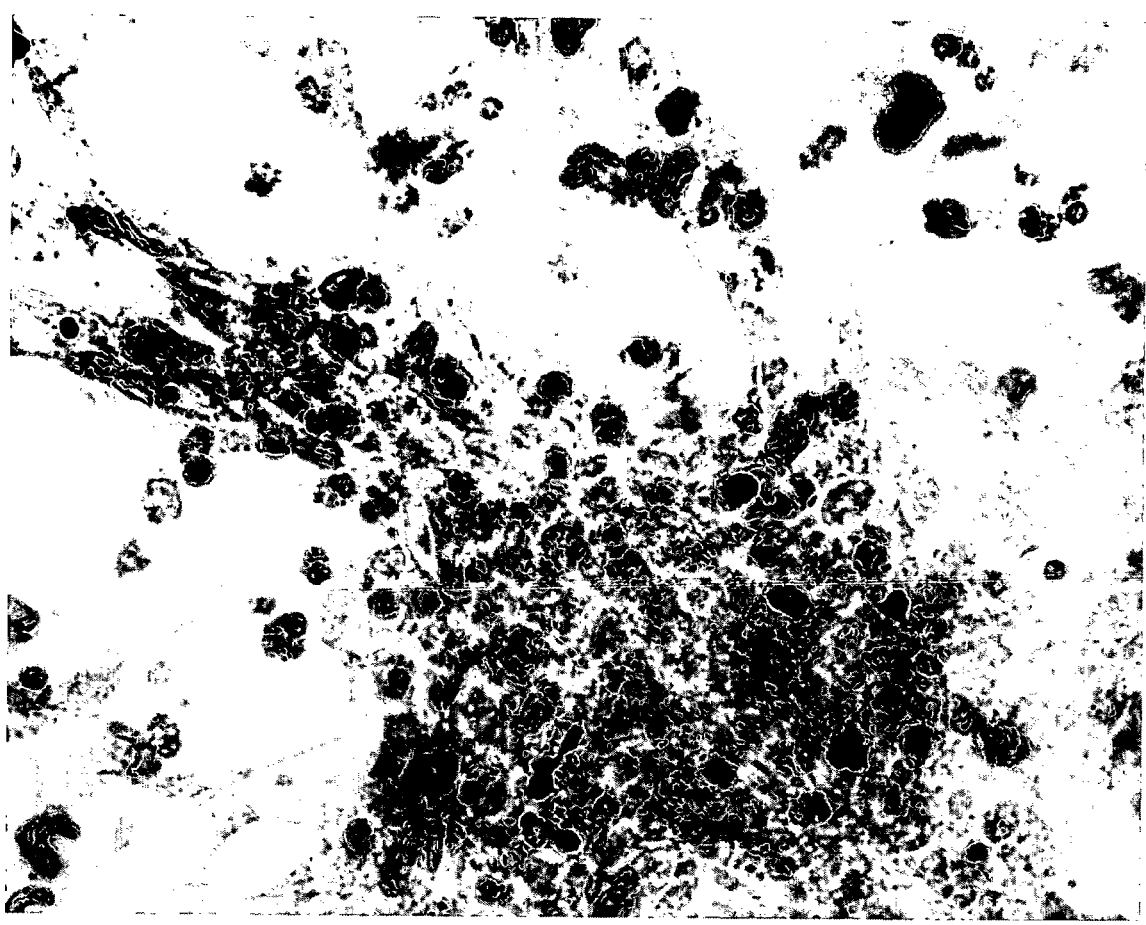
FIG. 9 is a photomicrograph showing a flat cluster of the NPC from M5 line. $Ca^{++}$ concentration of the culture medium at 0.1 mMol. 46% of the cells are BrDU-positive. 20× magnification.
Figure 10:
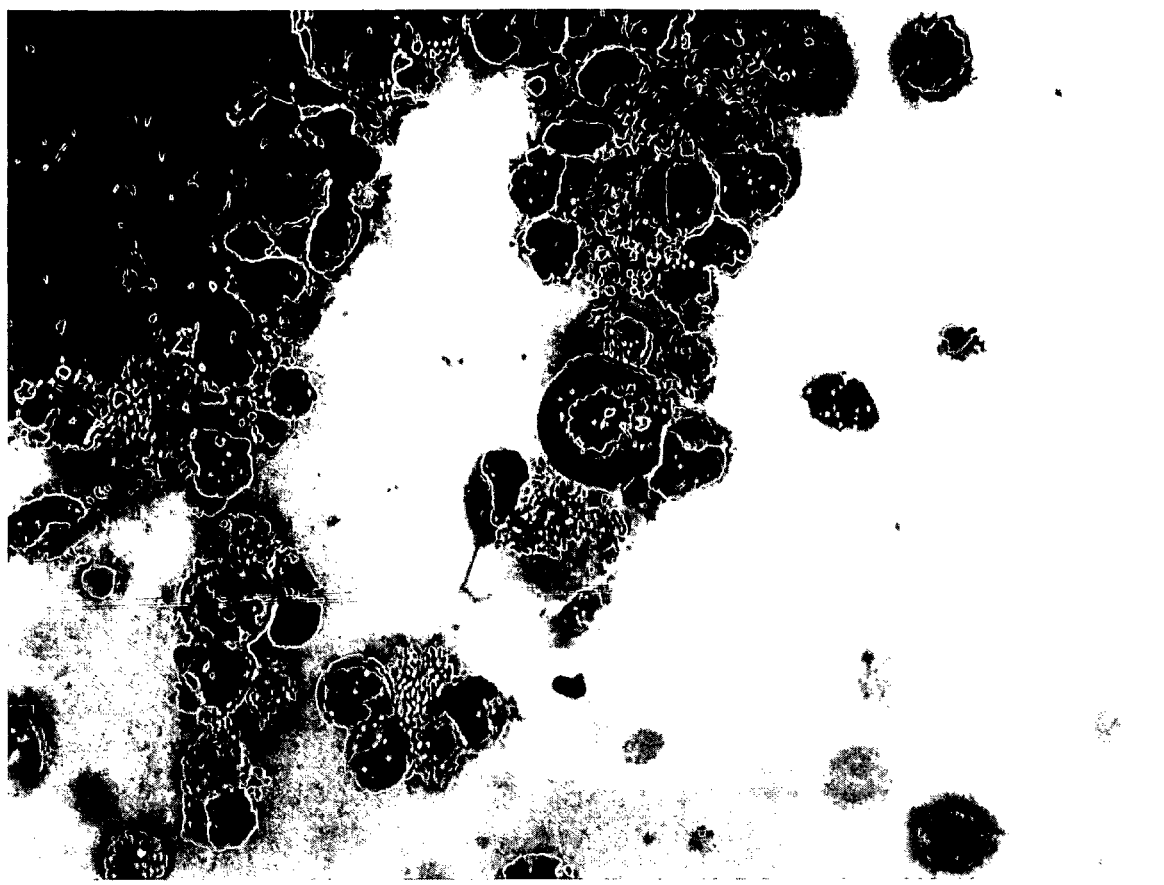
FIG. 10 is a photomicrograph showing a large floating cluster of cells from T5 line, with a mitotic figure in the center. Giemza stain. 40× magnification.
Figure 11:
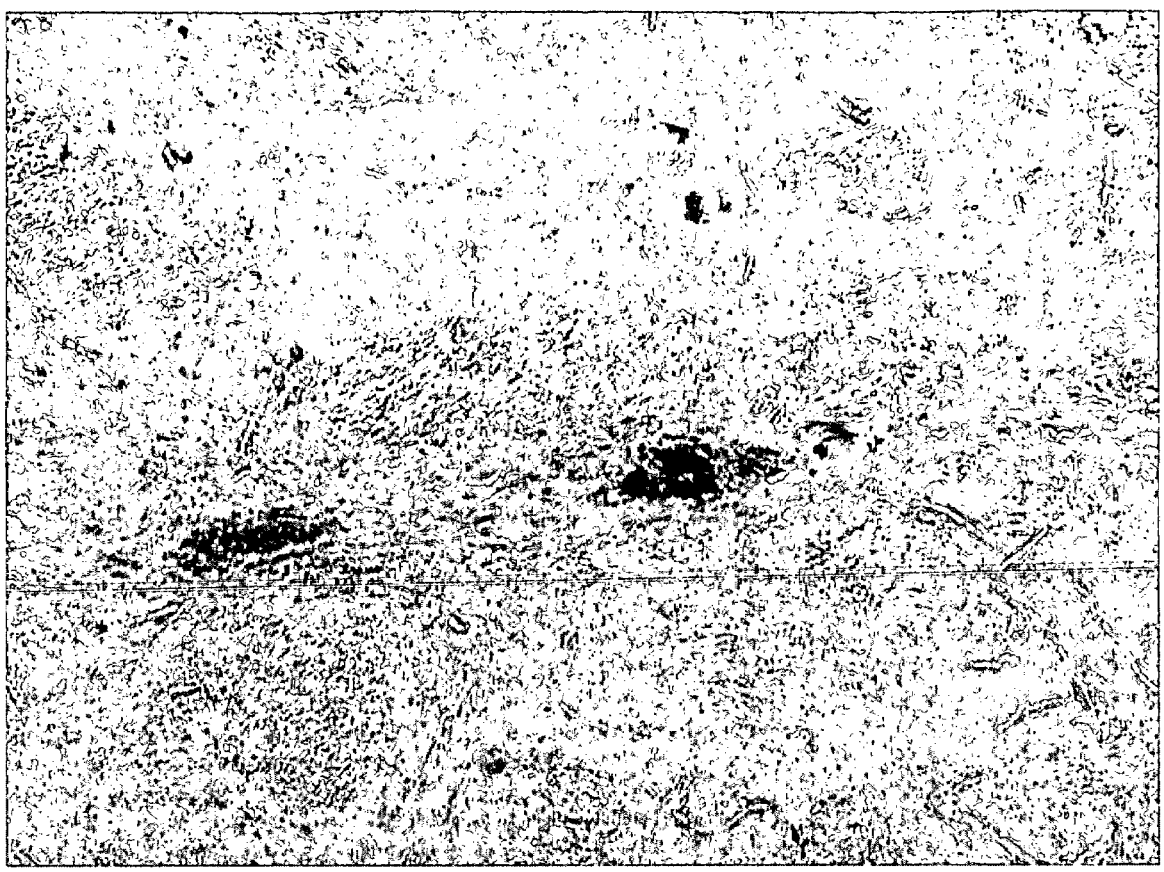
FIG. 11 is a photomicrograph showing the tyrosine hydroxylase (TH)-positive NPCs in the striatum of a 6-OHDA lesioned rat. 20× magnification.

The structure and function of NPC in culture is subject to manipulation via the culture medium. For example, raising the calcium concentration of the medium from 0.05 mM to 0.1 mM leads to attachment of the progenitor cells to the culture flask (see FIG. 7). The addition of LIF to the culture medium extends the doubling time, but allows for a higher population of neurons. Addition of LIF also helps to prevent formation of large clusters of NPC. TGFα in the medium serves to significantly reduce doubling time (e.g., from 14 days to 5 days). Accordingly, the culture medium is selected in accordance with the particular objectives, with some ingredients favoring growth and expansion and other ingredients favoring attachment and differentiation.

For general purposes, the cell culture requires a low calcium basal medium (e.g., $Ca^{++}$ free EMEM supplemented with calcium chloride), typically a B27 or equivalent supplement, and growth factors (e.g., EGF, FGF, TGFα). Optional ingredients include L-glutamine and LIF, which promote growth of neurons.

Example 3 below provides a detailed description of the optimization of culture media for expansion and for differentiation of NPC. In general, long-term growth and expansion requires a low calcium concentration. This is typically achieved by use of a calcium-free minimum essential medium (EMEM) to which calcium is added. Optimal growth and expansion has been observed at calcium concentrations of 0.05-0.06 mM. As the calcium concentration rises, e.g., above 0.15 mM, network formations between the neurons in culture are observed as they take on a more differentiated neuronal phenotype. In these higher calcium cultures, only 1-2% of the cells are immunopositive for the astrocytic marker GFAP, even without the addition of LIF to the culture medium.

NPC are typically grown in suspension cultures. Initial plating of primary cells was optimal at 30,000 to 50,000 cells/cm². Medium changes can be made every 6 days by removing the cells to a test tube and spinning (e.g., 5 min at 1,500 rpm). Typically, all but 2 ml of the original medium is discarded and the pellet is resuspended in the remaining 2 ml of original medium combined with an additional 3 ml of fresh medium. When density exceeds 400,000 cells/ml, the cells can be split into two culture vessels (e.g., T75 flasks). Trituration of the cells at the time of feeding helps to break up clusters of NPC and maintain their suspension in the culture medium. Those skilled in the art will appreciate that variation of these parameters will be tolerated and can be optimized to suit particular objectives and conditions.

The NPC of the invention can be used in therapeutic and diagnostic applications, as well as for drug screening and genetic manipulation. The NPC and/or culture media of the invention can be provided in kit form, optionally including containers and/or syringes and other materials, rendering them ready for use in any of these applications.

Cryopreservation of NPC

The invention provides optimized methods and media for freezing and thawing of NPC. The ability to store and successfully thaw NPC is valuable to their utility in clinical applications and ensuring a continued and consistent supply of suitable NPC. While most experts working with progenitor cell populations observe only a 1-2% survival of cells after freeze-thaw, the present invention offers media and methods that result in over 50% survival following freeze-thaw, with viability typically greater than 95%.

For cryopreservation, NPC are suspended in a low calcium medium supplemented with B27 and DMSO, and the trophic factors used in the expansion culture medium. Typically, the growth factors in the cryopreservation medium comprise about 20-100 ng/ml epidermal growth factor (EGF); about 10-50 ng/ml fibroblast growth factor basic (bFGF); and about 1-150 ng/ml transforming growth factor-alpha (TGFα). For thawing, both the culture medium and the flask, or other vessel into which the NPC will be grown, are pre-warmed to 15-40° C., preferably to approximately 25-37° C. Typically, culture flasks (or other vessel) are pre-warmed in an incubator with the same or similar gas, humidity and temperature conditions as will be used for growing the cells. For example, typical temperature is about 37° C. and typical $CO_2$ level is about 5% (and $O_2$ the remaining 95%).

Therapeutic Use of NPC

The NPC of the invention can be implanted into the central nervous system (CNS) of a host using conventional techniques. Neural transplantation or "grafting" involves transplantation of cells into the parenchyma, into the ventricular cavities or subdurally onto the surface of a host brain. Conditions for successful transplantation include: 1) viability of the implanted cells; 2) formation of appropriate connections and/or appropriate phenotypic expression; and 3) minimum amount of pathological reaction at the site of transplantation.

Therapeutic use of NPC can be applied to degenerative, demyelinating, excitotoxic, neuropathic and traumatic conditions of the CNS. Examples of conditions that can be treated via NPC grafts include, but are not limited to, Parkinson's disease (PD), Huntington's disease (HD), Alzheimer's disease (AD), multiple sclerosis (MS), amyotrophic lateral sclerosis (ALS), epilepsy, stroke, ischemia and other CNS trauma.

Methods for transplanting various neural tissues into host brains have been described in Neural Transplantation: A Practical Approach, S. B. Dunnett & A. Bjorklund (Eds.) Irl Pr; 1992, incorporated by reference herein. These procedures include intraparenchymal transplantation, i.e. within the host brain (as compared to outside the brain or extraparenchymal transplantation), achieved by injection or deposition of tissue within the host brain so as to be opposed to the brain parenchyma at the time of transplantation.

The procedure for intraparenchymal transplantation involves injecting the donor cells within the host brain parenchyma stereotactically. This is of importance if it is required that the graft become an integral part of the host brain and to survive for the life of the host. Typically, intraparenchymal transplantation involves pre-differentiation of the cells. Differentiation of the cells, however, limits their ability to migrate and form connections. Intraparenchymal transplantation of pre-differentiated cells is typically preferred when the objective is to achieve neurochemical production at the site of implantation.

Alternatively, the graft may be placed in a ventricle, e.g. a cerebral ventricle or subdurally, i.e. on the surface of the host brain where it is separated from the host brain parenchyma by the intervening pia mater or arachnoid and pia mater. For subdural grafting, the cells may be injected around the surface of the brain. In some embodiments, the NPC are injected intravenously. NPC introduced intraventricularly or intravenously will migrate to the appropriate region on the host brain. Intraventricular (or intravenous) transplantation is preferred when the objective is restoration of circuitry and function.

Injections into selected regions of the host brain may be made by drilling a hole and piercing the dura to permit the needle of a microsyringe to be inserted. The microsyringe is preferably mounted in a stereotaxic frame and three dimensional stereotaxic coordinates are selected for placing the needle into the desired location of the brain or spinal cord. For grafting, the cell suspension is drawn up into the syringe and administered to anesthetized graft recipients. Multiple injections may be made using this procedure. Examples of CNS sites into which the NPC may be introduced include the putamen, nucleus basalis, hippocampus cortex, striatum or caudate regions of the brain, as well as the spinal cord.

The cellular suspension procedure permits grafting of NPC to any predetermined site in the brain or spinal cord, is relatively non-traumatic, allows multiple grafting simultaneously in several different sites or the same site using the same cell suspension, and permits mixtures of cells having different characteristics. Multiple grafts may consist of a mixture of cell types, and/or a mixture of transgenes inserted into the cells. Preferably from approximately $10^4$ to approximately $10^8$ cells are introduced per graft. Optionally, the NPC can be grafted as clusters of undifferentiated cells. Alternatively, the NPC can be induced to differentiate prior to implantation.

For transplantation into cavities, which may be preferred for spinal cord grafting, tissue is removed from regions close to the external surface of the CNS to form a transplantation cavity, for example by removing glial scar overlying the spinal cord and stopping bleeding with a material such a gelfoam. Suction may be used to create the cavity. The stem cell suspension is then placed in the cavity.

Grafting of NPC into a traumatized brain will require different procedures. For example, the site of injury must be cleaned and bleeding stopped before attempting to graft. In addition, the donor cells should possess sufficient growth potential to fill any lesion or cavity in the host brain to prevent isolation of the graft in the pathological environment of the traumatized brain.

Genetically Modified NPC

The present invention provides methods for genetically modifying NPC for grafting into a target tissue site. In one embodiment, the cells are grafted into the CNS to treat defective, diseased and/or injured cells of the CNS. The methods of the invention also contemplate the use of grafting of transgenic NPC in combination with other therapeutic procedures to treat disease or trauma in the CNS or other target tissue. Thus, genetically modified NPC and/or PSC of the invention may be co-grafted with other cells, both genetically modified and non-genetically modified cells, which exert beneficial effects on cells in the CNS. The genetically modified cells may thus serve to support the survival and function of the co-grafted, non-genetically modified cells.

Moreover, the genetically modified cells of the invention may be co-administered with therapeutic agents useful in treating defects, trauma or diseases of the CNS (or other target tissue), such as growth factors, e.g. nerve growth factor (NGF), gangliosides, antibiotics, neurotransmitters, neuropeptides, toxins, neurite promoting molecules, and antimetabolites and precursors of these molecules, such as the precursor of dopamine, L-dopa.

Vectors carrying functional gene inserts (transgenes) can be used to modify NPC and/or PSC to produce molecules that are capable of directly or indirectly affecting cells in the CNS to repair damage sustained by the cells from defects, disease or trauma. In one embodiment, for treating defects, disease or damage of cells in the CNS, NPC are modified by introduction of a retroviral vector containing a transgene or transgenes, for example a gene encoding nerve growth factor (NGF) protein. The genetically modified NPC are grafted into the central nervous system, for example the brain, to treat defects, disease such as Alzheimer's or Parkinson's, or injury from physical trauma, by restoration or recovery of function in the injured neurons as a result of production of the expressed transgene product(s) from the genetically modified NPC. The NPC may also be used to introduce a transgene product or products into the CNS that enhance the production of endogenous molecules that have ameliorative effects in vivo.

Those skilled in the art will appreciate a variety of vectors, both viral and non-viral, that can be used to introduce the transgene into the NPC and/or PSC. Transgene delivery can be accomplished via well-known techniques, including direct DNA transfection, such as by electroporation, lipofection, calcium phosphate transfection, and DEAE-dextran. Viral delivery systems include, for example, retroviral vectors, lentiviral vectors, adenovirus and adeno-associated virus.

The nucleic acid of the transgene can be prepared by recombinant methods or synthesized using conventional techniques. The transgene may include one or more full-length genes or portions of genes. The polypeptides encoded by transgenes for use in the invention include, but are not limited to, growth factors, growth factor receptors, neurotransmitters, neuropeptides, enzymes, gangliosides, antibiotics, toxins, neurite promoting molecules, anti-metabolites and precursors of these molecules. In particular, transgenes for insertion into NPC include, but are not limited to, tyrosine hydroxylase, tryptophan hydroxylase, ChAT, serotonin, GABA-decarboxylase, Dopa decarboxylase (AADC), enkephalin, amphiregulin, EGF, TGF ($\alpha$ or $\beta$), NGF, PDGF, IGF, ciliary neuronal trophic factor (CNTF), brain derived neurotrophic factor (BDNF), neurotrophin (NT)-3, NT-4, and basic fibroblast growth factor (bFGF).

In general, polypeptides (including fusion proteins) and polynucleotides as described herein are isolated. An "isolated" polypeptide or polynucleotide is one that is removed from its original environment. For example, a naturally occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Treatment includes prophylaxis and therapy. Prophylaxis or therapy can be accomplished by a single direct injection at a single time point or multiple time points to a single or multiple sites. Administration can also be nearly simultaneous to multiple sites. Patients or subjects include mammals. The subject is preferably a human.

Administration and Dosage

The compositions are administered in any suitable manner, often with pharmaceutically acceptable carriers. Suitable methods of administering cells in the context of the present invention to a subject are available, and, although more than one route can be used to administer a particular cell composition, a particular route can often provide a more immediate and more effective reaction than another route.

The dose administered to a patient, in the context of the present invention, should be sufficient to effect a beneficial therapeutic response in the patient over time, or to inhibit disease progression. Thus, the composition is administered to a subject in an amount sufficient to elicit an effective immune response to the specific antigens and/or to alleviate, reduce, cure or at least partially arrest symptoms and/or complications from the disease or condition. An amount adequate to accomplish this is defined as a "therapeutically effective dose."

Routes and frequency of administration of the therapeutic compositions disclosed herein, as well as dosage, will vary from individual to individual, and may be readily established using standard techniques. Typically, the pharmaceutical compositions are administered by injection. Preferably, between 1 and 10 doses may be administered over a 52 week period. Alternate protocols may be appropriate for individual patients.

A suitable dose is an amount of a compound that, when administered as described above, is capable of promoting a therapeutic response, and is at least a 10-50% improvement relative to the untreated level. In general, an appropriate dosage and treatment regimen provides the material in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a tumor protein generally correlate with an improved clinical outcome. Such immune responses may generally be evaluated using standard proliferation, cytotoxicity or cytokine assays, which may be performed using samples obtained from a patient before and after treatment.

Pharmaceutical Compositions

The invention provides pharmaceutical compositions comprising NPC and/or PSC and, optionally, a physiologically acceptable carrier. Pharmaceutical compositions within the scope of the present invention may also contain other compounds that may be biologically active or inactive. For example, one or more biological response modifiers may be present, either incorporated into a fusion polypeptide or as a separate compound, within the composition.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, intracranial, intraventricular or subdural administration. Biodegradable microspheres (e.g., polylactate, polyglycolate) may also be employed as carriers for the pharmaceutical compositions of this invention. Suitable biodegradable microspheres are disclosed, for example, in U.S. Pat. Nos. 4,897,268 and 5,075,109. Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives.

EXAMPLES

The following examples are presented to illustrate the present invention and to assist one of ordinary skill in making and using the same. The examples are not intended in any way to otherwise limit the scope of the invention.

Example 1

Preparation of Progenitor Cells

This example demonstrates the preparation of brain progenitor cells (BPC), also referred to as neural progenitor cells (NPC). The BPC were derived from the telencephalon (T lines) and mesencephalon (M lines) of fetal brain. Fetal tissue was obtained from physicians in the local area using the guidelines recommended by the National Institutes of Health. The donor was approached with the request for tissue donation only after an elective abortion was performed, and informed consent was subsequently obtained. No monetary compensation or other incentive were offered to the patient, gynecologist, or clinic. A sample of maternal blood was obtained and the following serologic tests were performed: HIV, hepatitis A, B, and C, HTLV-1, VDRL, and CMV. Fetal brain tissue was obtained through a low-pressure aspiration technique under sterile conditions. There was no change in the indication, tuning, or methodology of the abortion between procedures. Fetal tissue immediately adjacent to the mesencephalon was cultured for aerobic and anaerobic bacteria, HSV, and CMV. Microscopic diagnosis was also performed using Gram stain. Fetal tissue from donors with a history of genital herpes, cancer, asthma, lupus, rheumatoid arthritis, allergies, vasculitis of autoimmune origin, drug abuse, or prostitution was excluded.

Gestation of the fetal cadaver was determined according to crown-to-rump length (CRL) as measured by ultrasound. The gestational age ranged from 6 to 8 weeks (CRL 20 to 24 mm). The samples of telencephalon and mesencephalon were obtained from 2 donors (CRL: 20 and 24 mm). Dissections were carried out at 4° C. in a laminar flow hood (Environmental Air Control, Inc.), under a dissecting microscope (Leica, Wild MJZ, Meerbrugg, Switzerland). A general purpose serum-free medium (Ultraculture, Whittaker Bioproducts) was used, with the addition of, 5 mmol of L-glutamine and 10 µg/ml of Kanamycin and 0.25 µg/ml of Fungizone. The fetal tissue was rinsed ten times with the culture medium, and then the brain was stripped of cartilaginous skull and the meninges and transferred to Hank's Balanced Salt Solution (HBSS) supplemented with 10 µg/ml of Kanamycin sulfate and 0.25 µg/ml of Fungizone for microdissection. The dorsal cortex from both hemispheres (telencephalon) was removed parasagittally. Further, the rostral half of ventral mesencephalon and tectum was dissected. Collected samples were thoroughly minced with microscissors and triturated using sterile fire-polished pipettes. No prior trypsinization was used. Before plating cells to culture flasks or onto glass chambered slides, the cell viability (Trypan Blue exclusion test) and density were assessed. Average viability was 96%. The optimal plating density was found to be 30,000 to 50,000 cells/$cm^2$.

Example 2

Characterization of Source Tissue

This example describes the characterization of tissue dissected for the above preparation of BPC. Areas of the fetal brain tissue adjacent to the dissected tissue were treated similarly and fixed for immunocytochemistry and electron- and light microscopy. These adjacent sections were analyzed retrospectively for viability and functional specificity.

For morphological analysis, cortex and mesencephalon were taken from the fetus and processed for immunocytochemistry or ultrastructural morphology. Following dissection, part of the tissue was fixed in 4% buffered (pH 7.4) PFA fixative, then embedded in paraffin and sectioned on a rotary microtome. Samples of this tissue were processed in a histochemical procedure to visualize the various neuronal and glial markers (AchE, TH, NSE, MAP2, BrDU, Nestin, etc.).

Immunocytochemical labeling with peroxidase reaction was carried out with antibodies to the glial marker glial fibrillary acidic protein (GFAP; Lipshaw, Philadelphia, Pa.), the neurotransmitter GABA (Sigma Chemical Co., St. Louis, Mo.), and a dopaminergic marker, the catecholaminergic synthesis enzyme TH (Sigma Chemical Co., St. Louis, Mo.). Briefly, sections were deparaffinized and rehydrated in a descending series of ethanol baths, then incubated in 3% hydrogen peroxide blocking solution (Signet Laboratories, Dedham, Mass.). The primary antibody was applied onto the slides, and then removed with two rinses of phosphate-buffered saline. Slides were then incubated in linking reagent and then labeling reagent, then visualized with AEC chromogen (Signet Laboratories, Dedham, Mass.). For electron microscopy, the tissue was fixed in Karnovsky's fixative, postfixed in 1% osmium tetroxide, dehydrated through a series of ethanols and propylene oxide, then embedded in Medcast resin (Ted Pella, Redding, Calif.). Ultrathin sections were collected on copper grids, stained with lead and uranium and viewed with a JEOL-100CX electron microscope.

After two to four passages, most of the cultured cells were harvested and frozen in liquid Nitrogen. Cryo medium contains the expansion culture medium with 10% DMSO, 4% of B-27 supplement, and 5 to 7 µl/ml of MEM non-essential amino acids solution (Gibco, NY).

Example 2A

Staining for Glial Fibrillary Associated Protein (GFAP)

Cells were plated onto SUPERFROST PLUS slides using Cytospin® centrifuge (ThermoShandon, Pittsburgh, Pa.) and then fixed in 4% paraformaldehyde for 20 min at room temperature. The cells were washed twice for 5 min with 1.times.PBS, pH 7.4 (Gibco). Cells were permeabilized overnight with 70% methanol at 4.degree. C. The cells were washed twice for 5 min in 1×PBS, then blocked for non-specific binding with SuperBlock™ blocking buffer (Pierce Biotechnology, Rockford, Ill.) for 60 mm at room temperature. The SuperBlock was shaken off the slides, and cell preparations were incubated overnight at room temperature with primary monoclonal, mouse derived antibodies to human specific glial fibrillary acidic protein (GFAP) (VectorLaboratories, Inc. Burlingame, Calif.) diluted in SuperBlock™ buffer with 0.1% Triton-X-100. The cells were washed twice for 5 mm in 1.times.PBS. Cellular endogenous peroxidase activity was blocked with ImmunoPure Peroxidase Suppressor™ (Pierce Biotechnology, Rockford, Ill.) for 20 min at room temperature. The cells were washed twice for 5 min in 1×PBS and incubated for 120 min at room temperature with biotinylated secondary antibody (VectorLaboratories, Inc. Burlingame, Calif.) specific to primary antibodies derived from a mouse host (Biotinylated anti-mouse IgG, affinity purified, rat adsorbed) diluted in SuperBlock™ buffer with 0.1% Triton-X-100. Then the cells were washed twice for 5 min in 0.1M and incubated with tertiary peroxidase-conjugated streptavidin specific to biotin (Vectastain Elite ABC reagent, VectorLaboratories) for 60 min at room temperature. The cells were washed twice for 5 min in 1×PBS and incubated with diaminobenzidine (VectorLaboratories, Inc.) for 2 min at room temperature. All these steps were performed using a humidity chamber. The cells were washed three times for 1 min in room temperature tap water and counterstained with Hematoxylin QS (VectorLaboratories, Inc. Burlingame, Calif.) for 30 sec. The cells were washed three times for 1 min in room temperature tap water, treated with bluing reagent (Richard-Allen Scientific,) for 30 sec at room temperature, washed three times for 1 min in warm tap water and cover slipped with glycergel (DakoCytomation, Carpinteria, Calif.) and stored at room temperature in the dark.

Example 2B

Staining for 5-Bromodeoxyuridine (BrDU)

The cells were plated onto Superfrost Plus™ slides using Cytospin® centrifuge(Thermo Shandon, Pittsburgh, Pa.) and then fixed in 4% paraformaldehyde for 20 min at room temperature. The cells were washed twice for 5 min with 1.times.PBS, pH 7.4 (Gibco) permeabilized overnight with 70% methanol at 4° C., washed twice for 5 min in 1.times.PBS and treated with SuperBlock™ blocking buffer (Pierce Biotechnologies, Inc., Rockford, Ill.) for 60 min at room temperature to prevent non-specific binding. The SuperBlock was shaken off each slide, which was then incubated overnight at 1.times.PBS. The endogenous peroxidase activity was quenched with ImmunoPure Peroxidase Suppressor™ (Pierce Biotechnologies) for 20 min at room temperature. Slides were washed twice for 5 min in 1× room temperature with primary monoclonal mouse derived antibodies to BrDU (VectorLaboratories, Inc.) diluted in Super-Block™ buffer with 0.1% Triton-X-100. Then the slides were washed twice for 5 min in PBS and incubated for 120 min at room temperature with secondary biotinylated anti-mouse IgG, affinity purified, rat adsorbed (VectorLaboratories, Inc) antibodies diluted in SuperBlock™ buffer with 0.1% Triton-X-100 and specific to primary antibodies. After this step, the cells were washed twice for 5 min in 1.times.PBS and incubated with tertiary peroxidase-conjugated streptavidin specific to biotin (Vectastain Elite ABC reagent from Vector-Laboratories) for 60 mm at room temperature. Then the cells were washed twice for 5 min in 1.times.PBS and incubated with diaminobenzidine (VectorLaboratories, Inc.) for 2 min at room temperature. Finally, the cells were washed three times for 1 mm in room temperature tap water, counterstained with Hematoxylin QS (Vector) for 30 sec, washed three times for 1 mm in room temperature tap water treated with bluing reagent (Richard-Allen Scientific) for 30 sec at room temperature, washed three times for 1 mm in warm tap water, cover slipped with glycergel (DakoCytomation, Carpinteria, Calif.) and stored at room temperature in the dark.

Example 2C

Staining for Neuron Specific Enolase (NSE)

The cells were plated onto Superfrost Plus™ slides using Cytospin® centrifuge (Thermo Shandon, Inc., Pittsburgh, Pa.) and then fixed in 4% paraformaldehyde for 20 mm at room temperature. The slides were washed twice for 5 min with 1.times.PBS, pH 7.4 (Gibco), permeabilized overnight with 70% methanol at 4° C., washed twice for 5 min in 1×PBS and treated with SuperBlock™ blocking buffer (Pierce Biotechnology, Inc., Rockford, Ill.) for 60 min at room temperature to prevent non-specific binding. The SuperBlock was allowed to run off the slides, which were then incubated with primary monoclonal mouse derived antibodies to human NSE (Chemicon) diluted in SuperBlock™ buffer with 0.1% Triton-X-100 for 30 min at room temperature.

The cells were rinsed twice for 5 min with 1.times.PBS, then the endogenous peroxidase activity was suppressed with ImmunoPure Peroxidase Suppressor™ (Pierce Biotechnology) for 20 min at room temperature. The cells were washed twice for 5 min in 1.times.PBS and incubated with secondary biotinlyated antibodies specific to primary antibodies derived from a mouse host (biotinylated anti-mouse IgG, affinity purified, rat adsorbed) diluted in SuperBlock™ buffer with 0.1% Triton-X-100 for 120 min at room temperature. The cells were washed twice for 5 min in 1.times.PBS and incubated with tertiary peroxidase conjugated streptavidin specific to biotin (Vectastain Elite ABC reagent from Vector-Laboratories) for 60 min at room temperature. After this, the cells were washed twice for 5 min in 1.times.PBS, incubated with diaminobenzidine (VectorLaboratories, Inc.) for 2 min at room temperature, washed three times for 1 mm in room temperature tap water, counterstained with Hematoxylin QS (VectorLaboratories, Inc) for 30 sec., washed again three times for 1 min in room temperature tap water, treated with bluing reagent (Richard-Allen Scientific) for 30 sec at room temperature, washed three times for 1 mm in warm tap water, cover slipped with glycergel (DakoCytomation, Carpinteria, Calif.) and stored at room temperature in the dark.

Example 2D

Staining for CD 34

Cells were plated onto Superfrost Plus™ slides via Cytospin® centrifuge (Thermo Shandon) and then fixed in 4% paraformaldehyde for 20 min at room temperature. The cells were washed twice for 5 mm with 1.times.PBS, pH 7.4 (Gibco). Cells were permeabilized overnight with 70% methanol at 4° C. The cells were washed twice for 5 min 1.times.PBS. Cells were blocked for non-specific binding with SuperBlock™ blocking buffer (Pierce) for 60 mm at room temperature and covered. The SuperBlock was allowed to run off, and cell preparations were incubated with primary antibody to human CD 34 (Human specific CD 34 monoclonal mouse derived antibody; DakoCytomation, Carpinteria, Calif.) diluted in SuperBlock™ buffer with 0.1% Triton-X-100 overnight at room temperature. The cells were washed twice for 5 min in 1.times.PBS.

Endogenous peroxidase activity was suppressed with ImmunoPure Peroxidase Suppressor™ (Pierce) for 20 min at room temperature then washed twice for 5 min in 1.times.PBS. Cell preparations were incubated with Biotinylated secondary antibody specific to primary antibodies derived from a mouse host (Biotinylated anti-mouse IgG, affinity purified, rat adsorbed; Vector) diluted in SuperBlock™ buffer with 0.1% Triton-X-100 for 120 min at room temperature and covered. The cells were washed twice for 5 min in 1.times.PBS. Cell preparations were incubated with tertiary peroxidase-conjugated streptavidin specific to biotin (Vectastain Elite ABC reagent; Vector) for 60 min at room temperature and covered. The cells were washed twice for 5 min in 1.times.PBS. Cell preparations were incubated with peroxidase enzyme substrate solution (diaminobenzidine; Vector) for 2 min at room temperature. The cells were washed three times for 1 min in room temperature tap water. Cells were counterstained with Hematoxylin QS (Vector) for 30 sec. The cells were washed three times for 1 min in room temperature tap water. For sharpness, cells were incubated with bluing reagent (Richard-Allen Scientific) for 30 sec at room temperature. The cells were washed three times for 1 min in warm tap water. The cell preparations were cover slipped with glycergel (DakoCytomation, Carpinteria, Calif.) and stored at room temperature in the dark.

Example 2E

Staining for Leukocyte Common Antigen (CD 45)

The cells were plated onto Superfrost Plus™ slides using Cytospin® centrifuge (Thermo Shandon) and then fixed in 4% paraformaldehyde for 20 min at room temperature. The cells were washed twice for 5 mm with 1.times.PBS, pH 7.4 (Gibco), permeabilized overnight with 70% methanol at 4° C., and washed twice for 5 mm in 1.times.PBS. The non-specific binding was blocked with SuperBlock™ blocking buffer (Pierce) for 60 min at room temperature, then incubated for 30 min at room temperature with primary human specific anti-leukocyte common antigen monoclonal mouse derived (DakoCytomation) antibodies to human CD 45, diluted in SuperBlock™ buffer with 0.1% Triton-X-100.

The cells were washed twice for 5 min in 1.times.PBS, then endogenous peroxidase Activity was quenched with ImmunoPure Peroxidase Suppressor™ (Pierce) for 20 min at room temperature. After this, the cells were washed twice for 5 mm in 1.times.PBS, and incubated for 120 mm at room temperature with biotinylated secondary antibodies diluted in SuperBlock™ buffer with 0.1% Triton-X-100 (biotinylated anti-mouse IgG, affinity purified, rat adsorbed from Vector Laboratories, Inc.) specific to primary antibodies derived from a mouse host. The cells were washed twice for 5 min in 1.times.PBS, incubated with tertiary peroxidase-conjugated streptavidin specific to biotin (Vectastain Elite ABC reagent from Vector Laboratories, Inc) for 60 min at room temperature, washed twice for 5 mm in 1.times.PBS and incubated with diaminobenzidine (Vector Laboratories, Inc) for 2 min at room temperature. Finally, the cells were washed three times for 1 min in room temperature tap water, with Hematoxylin QS (Vector Laboratories, Inc) for 30 sec., washed three times for 1 min in room temperature tap water, treated for sharpness with bluing reagent (Richard-Allen Scientific) for 30 sec at room temperature, washed three times for 1 min in warm tap water, covered slipped with glycergel (DakoCytomation, Carpinteria, Calif.) and stored at room temperature in the dark.

This staining protocol was also used with antibodies to Oct-4 (Chemicon), beta tubulin class III (Serotec), nestin (R&D Systems), tyrosine hydroxilase (Chemicon), and human mitochondria (Chemicon).

Example 3

Optimization of Culture Media

This example describes the various media components tested for their influence on expansion and differentiation of BPC. Growth rates of the telencephalon- and mesencephalon-derived BPC were compared in three standard culture media: Dulbecco's Modification of Eagle's Medium (DMEM); Eagle's Minimum Essential Medium (EMEM) without calcium (Biowhittaker), Neurobasal (GibcoBRL), Ultraculture (Biowhittaker), and PFMR-4+8F (BRF) with at least 25 variable combinations of mitogens bFGF, EGF, TGFα, LIF; Caspase 3 and 8 inhibitors; and B-27 supplement. The efficacy of each combination was tested by cell viability and doubling time during short- and long-term expansion, as well as behavioral effects in the rat PD model after intra-striatal transplantation. The EMEM-based, low calcium culture medium with addition of bFGF, EGF, TGFα, LIF, and B-27 presented with the best results.

After the numerous ingredients were tested, perhaps the most surprising result was the lack of benefit upon addition of the caspace-1 inhibitor, either acetyl-Tyr-Val-Ala-Asp (Ac-YVAD) or acetyl-Tyr-Val-Ala-Asp chloromethyl ketone (Ac-YVAD-CMK) (Calbiochem). In fact, the presence of caspace inhibitor in the growth medium was associated with decreased cell counts. In addition, no benefit was observed with the use of interleukin-1 (IL-1). Glial cell line-derived neurotrophic factor (GDNF) and ciliary neurotrophic factor (CTNF) were both found to prompt rapid differentiation and cell death.

Transforming growth factor alpha (TGFα) was found to shorten doubling time significantly (e.g., from 14 days to 5 days). Leukemia inhibitory factor (LIF) promoted neuronal cells and prevented the formation of large clusters of NPC. Basic fibroblast growth factor (bFGF) resulted in good proliferation, even when used in the absence of other trophic factors. Epidermal growth factor (EGF) alone did not support robust growth, but when combined with bFGF and TGFα, optimal growth was observed.

Cells grown in bFGF as the sole trophic factor were compared to NPC grown in medium containing EGF+BFGF+TGFα (E+F+T). Two million cells per animal were transplanted into PD rats (an animal model for Parkinson's disease). At 6 days post-transplant, the bFGF only cells showed a 12% decrease in density, while the E+F+T cells exhibited an increase in density of 167%.

Progenitor Expansion Medium

Basal Medium:
Eagle's Minimum Essential Medium (EMEM) without calcium, BioWhittaker, Inc., Walkersville, Md., cat #06-1746.

Supplements:
B27 (2%), Gibco BRL, cat# 17504
r-hEGF (20 ng/ml), Peprotech, cat# 100-15
r-hFGF basic (bFGF, FGF2), (20 ng/ml), Peprotech, cat#100-18B
Sodium Pyruvate (0.11 mg/ml), Sigma, cat# S-8636
Calcium Chloride $2H_2O$, (0.1 mM), Sigma, cat#C-7902

Optional:
Gentamicin (50 µg/ml), Sigma, cat#G-1272
Amphotericin B (1.25 µg/ml), Sigma, cat#A-2942
or Sigma's 100×antibiotic/antimycotic, cat#A-9909

Progenitor Differentiation Medium

Basal Medium:
PFMR-4+8F, Biological Research Faculty and Facility, Inc (BRFF), cat#SF-240
Or DMEM, Neurobasal, or EMEM without calcium (brought up to 0.1 mM $CaCl_2$)

Differentiation Factors:
Glial Cell-Derived Neurotrophic Factor (GDNF) (10 ng/ml), Sigma, cat# G-1777
IL-1alpha, (100 pg/ml), Sigma, cat# I-2778
IL-11 (1 ng/ml), Sigma, cat# I-3644
Leukemia Inhibitory Factor (LIF), (1 ng/ml), Sigma, cat# L-5283
$N^6$,2'-O-Dibutyryladenosine 3',5'-cyclic monophosphate (db-cAMP), (100 µM), Sigma, cat#D-0627
Forskolin (5 µM), Calbiochem-Behring Corp, cat#344270

Optional:
0.25 µg/ml fungizone
10 µg/ml kanamycin sulfate

Media Preparation:
Glutamate, when added to medium, is used only to provide for initial plating—subsequent feedings use medium without glutamate.

Expansion Medium

| Formulation | Recipe | Notes |
| --- | --- | --- |
| 95.5 ml basal medium | 97.5 ml basal medium | Calcium-free EMEM preferred for progenitor cell expansion; for differentiation, can use EMEM, DMEM or Neurobasal |
| 0.05 mM $CaCl_2$ | 120 ul/100 ml | Only added to calcium-free EMEM; adjust quantity for expansion vs. differentiation |
| 2% B27 supplement | 2.0 ml B27 | |

-continued

| Formulation | Recipe | Notes |
| --- | --- | --- |
| 0.5 mM L-glutamine | 0.25 ml 200 mM L-glutamine (29.2 mg/ml) | Promotes growth of neurons over glia, who prefer 2 mM L-glutamine 0.5 mM L-glutamine = 73 mg/L 100 ml med. = 7.3 mg = 0.25 ml 200 mM L-glutamine |
| 2 μg EGF (20 ng/ml) | 2 × 25 μl aliquot (40 ng/μl EGF) | |
| 1 μg FGF (10 ng/ml) | 1 × 25 μl aliquot (40 ng/μl FGF) | |
| 1 μg TGFα (10 ng/ml) | 1 × 25 μl aliquot (40 ng/μl TGFα) | |

Differentiation Medium

| Recipe | Formulation | Notes |
| --- | --- | --- |
| 97.5 ml basal medium | 97.5 ml EMEM without calcium | BioWhitaker Cat#06-174G |
| 2.0 ml B27 | 2% B27 supplement | |
| 1 ml 11 mg/ml Na pyruvate | 0.11 mg/ml sodium pyruvate | |
| 40 μl 25 mM $CaCl_2$ | 0.1 mM $CaCl_2$ | |
| 50 μl EGF (2 aliquots @40 ng/μl) | 2 μg EGF; 20 ng/ml EGF | |
| 50 ul bFGF (2 aliquots @40 ng/μl) | 2 μg FGF; 20 ng/ml FGF | |
| 25 ul TGFα (1 aliquot @40 ng/μl) | 1 μg TGF; 10 ng/ml TGF | |
| 100 μl LIF | 1 μg LIF; 10 ng/ml LIF | |

Neurobasal medium:

| Formulation | Recipe | Notes |
| --- | --- | --- |
| 97.5 ml Neurobasal medium | 97.5 ml Neurobasal medium | |
| 2% B27 supplement | 2.0 ml B27 | |
| 0.5 mM L-glutamine | 0.25 ml 200 mM L-glutamine (29.2 mg/ml) | Promotes growth of neurons over glia, who prefer 2 mM L-glutamine |
| 25 μM L-Glutamic acid | 184 μl 2 mg/ml L-glutamic acid (20 mg L-Glu + 10 ml ddH20) | Helps cells attach |
| 2 μg EGF (20 ng/ml) | 2 × 25 μl aliquot @40 ng/μl | |
| 1 μg FGF (10 ng/ml) | 1 × 25 μl aliquot @40 ng/μl | |
| 1 μg TGFα (10 ng/ml) | 1 × 25 μl aliquot @40 ng/μl | |

Once made, this medium keeps 1-2 weeks refrigerated.

Example 4

Features of NPC Cultured in Media of the Invention

The NPC cultured in the medium of the invention have been shown to have the characteristics of neural progenitor cells: they can be maintained indefinitely in EMEM culture, show positive staining for BrDU, express Nestin, under low [$Ca^{++}$] conditions they are capable of generating dopaminergic (35-60%) and serotonergic (24-40%) neurons as well as a number of other MAP2 positive cells (10-12%), and glia (GFAP positive cells 15-23%). They also sporadically generate nucleated red cells (2-3%) in vitro and myoblasts when injected into the ischemic rat heart.

In contrast, NPC will remain in suspension and undifferentiated when cultured in the low calcium medium EMEM of the invention. As the calcium concentration is raised, e.g., to 0.1 mM, then the NPC form networks and exhibit a neuronal phenotype. Even without the addition of LIF to favor neurons over glia, only 1-2% of these cultured cells are immunopositive for the glial marker GFAP, suggesting that the population is primarily neuronal.

Example 5

Transplantation of NPC into Brain in an Animal Model of Parkinson's Disease

This example demonstrates that NPC prepared in accordance with the invention can be successfully grafted into rat brain. The example shows that grafted cells can exhibit normal differentiation into tyrosine hydroxylase (TH) positive cells. In addition, the results show that the grafted NPC ameliorate the behavioral deficit characteristic of this animal model of Parkinson's disease.

For implantation, free-floating NPC are removed from the culture flask and spun as is done for medium changes. The pellet is re-suspended in the remaining 2 mls of medium, and this concentrated suspension is counted on a hemacytometer. Additional medium is added to bring the final cell concentration to 350,000 cells/μl.

The substantia nigra was lesioned via injection of 4 μl (8 μg) 6-hydroxydopamine, 6-OHDA (Research Biomedicals International, Mass.) using a Hamilton syringe (Hamilton Co., Nevada). The injection was carried out over 2 minutes, with a three minute wait after injection to allow diffusion before removal of the needle.

Two weeks following nigral lesion, rats were placed under general anesthesia (Ketamine 87 mg/kg and Xylazine 10 mg/kg; or 4% isoflurane gas) and fixed in a stereotaxic apparatus. The scalp incision was made and a hole was drilled in the skull at the coordinates of the striatum. The progenitor cells were implanted using a Hamilton syringe (70,000 cells/2 μl per animal) into the striatum ipsilateral to the 6-OHDA lesion, at stereotaxic coordinates A=−0.11; L=3.8; V=4.5. The incision was then closed and treated with Betadine. All NPCs were implanted without prior conditioning.

For rotational behavior testing, rats were injected subcutaneously with amphetamine or vehicle. Immediately after injection, animals were placed in a locomotor chamber measuring 3 feet by 3 feet (Columbus Instruments, Columbus, Ohio). Following a two-minute adjustment period, all rotations were tracked by a CCD camera mounted over the chamber and analyzed by the Videomex V™ video image analyzer (Columbus Instruments, Columbus, Ohio). Locomotor activity and rotation were recorded for 60 minutes.

Both groups of animals that received T5 or M5 cells showed significant and comparable reduction in their rotational behavior. In both groups of animals, about 14-24% of the NPCs differentiated into TH-positive cells.

Example 6

NPC Implanted in Substantia Nigra Become Tyrosine Hydroxylase Positive

NPC, both M5 and T5 cells, were implanted using a method similar to that described in Example 5 above. The M5 cell population, derived from brainstem, was 24-30% positive for tyrosine hydroxylase (TH) prior to implantation. After implantation, 54% of the M5 NPC were TH positive. The T5 cells, derived from forebrain, were all TH negative in culture. Once implanted, 32% of the implanted NPC were TH positive.

Example 7

Differentiation of NPC

Culture conditions as described above were varied and manipulated to determine the optimal conditions to induce differentiation of NPC. The resulting optimized differentiation medium contains 0.15 mM Ca++, 0.5 mM L-glutamine, 10 ng/ml GDNF, 15 ng/ml retinoic acid.

Example 8

Cryopreservation of NPC

Media ingredients were varied and manipulated to determine the optimal conditions for cryopreservation of NPC. B27, in addition to DMSO, appears to provide a significant protective effect contributing to the exceptionally high viability observed in thawed NPC.

For cryopreservation, NPC were suspended in a low calcium medium (0.06 mM $Ca^{++}$ EMEM) supplemented with 2% B27, LIF (15 ng/ml), EGF (50 ng/ml), FGF and TGF (25 ng/ml) and 10% DMSO. The cells are first placed in a freezer at about –40° C. for 1 to 1.5 hours, after which they are stored in liquid nitrogen. Cells can be stored at below about –80° C., typically at about –200° C. The liquid nitrogen storage tank used in these studies is maintained at –197° C.

For thawing, both the culture medium and the flask was pre-warmed to 37° C. in a water bath at 37° C. Using this cryopreservation method, over 95% viability is consistently observed in the NPC upon thawing (using dye exclusion cell counts). Typically, the cells appear shrunken and of abnormal morphology for the first 5-7 days after thawing. Despite this appearance, the cells are able to exclude trypan blue dye. After about one week, the cells recover to their pre-freezing state, exhibiting typical morphology, growth and doubling times.

Example 9

Pluripotent Stem Cells in Cultures of the Invention

Cells cultured as described above for NPC have been evaluated for expression of the stem cell marker Oct4. Oct4 is a transcription factor that is specifically expressed in embryonic and adult stem cells and tumor cells, but not in cells of differentiated tissues (Tai et al., Carcinogenesis, published online Oct. 28, 2004). Oct4-positive cells are also capable of developing in culture into oogonia that enter meiosis, recruit adjacent cells to form follicle-like structures, and later develop into blastocysts (Hubner, K. et al., Science, 2003, 300(5623):1251-6). This capacity for oogenesis in culture makes them useful for nuclear transfer and manipulation of the germ line, and as well as to create models for studies on fertility treatment and germ and somatic cell interaction and differentiation.

Cells cultured as described above for NPC, by six weeks in culture, will show some stem cells (OCT4-positive), and mostly nestin-positive progenitor cells. Over a period of four months in culture, the population shifted from containing about 5% Oct4-positive cells to about 30% Oct4-positive cells. This observation could indicate that these cells de-differentiate in long-term culture. Alternatively, this may reflect a selective survival of stem cells in long-term culture.

Figure 17:
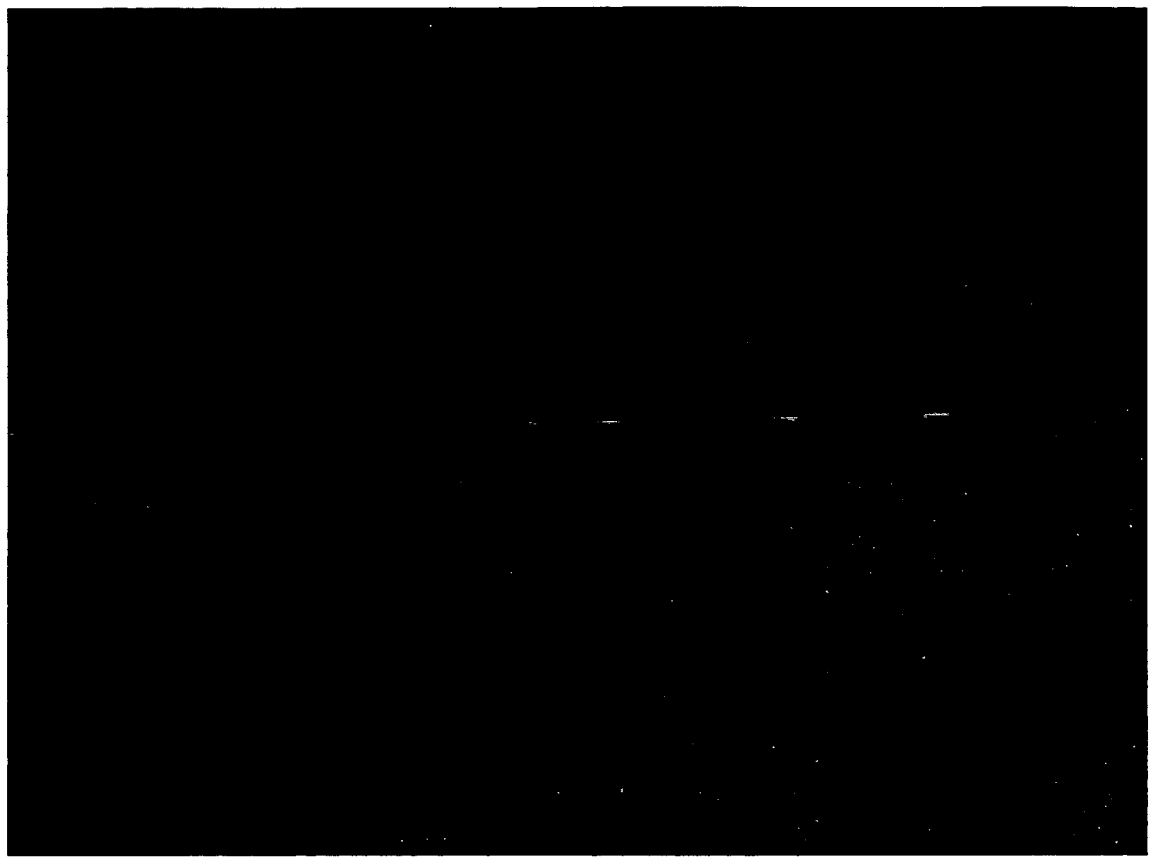
FIG. 17 is a photomicrograph showing co-expression of nestin and Oct-4 in the same NPCs, green fluorescence representing Oct-4 and red representing nestin. 20×.

Oct4-positive cells were also observed to co-express the NPC marker, nestin, as shown in FIG. 17. Nestin-positive cells are thus capable of differentiating into neural cells, but not necessarily committed to this path.

Example 10

Intraventricular NPCs Restore Function in Animal Model of Parkinson's Disease

Nigral lesions were performed in rats as described above in Example 5 to create the rotational behavior deficit characteristic of this rat model of Parkinson's disease. 500,000 human NPC prepared as described above were injected into the cerebral ventricle. After completion of rotational behavior studies, which confirmed successful amelioration of rotational behavior, tissues sections were prepared for immunohistochemical examination. Human cells from the implanted NPCs were found to have migrated to neural structures including the striatum, substantia nigra and hippocampus, and to differentiate into neurons and glia.

Figure 18:
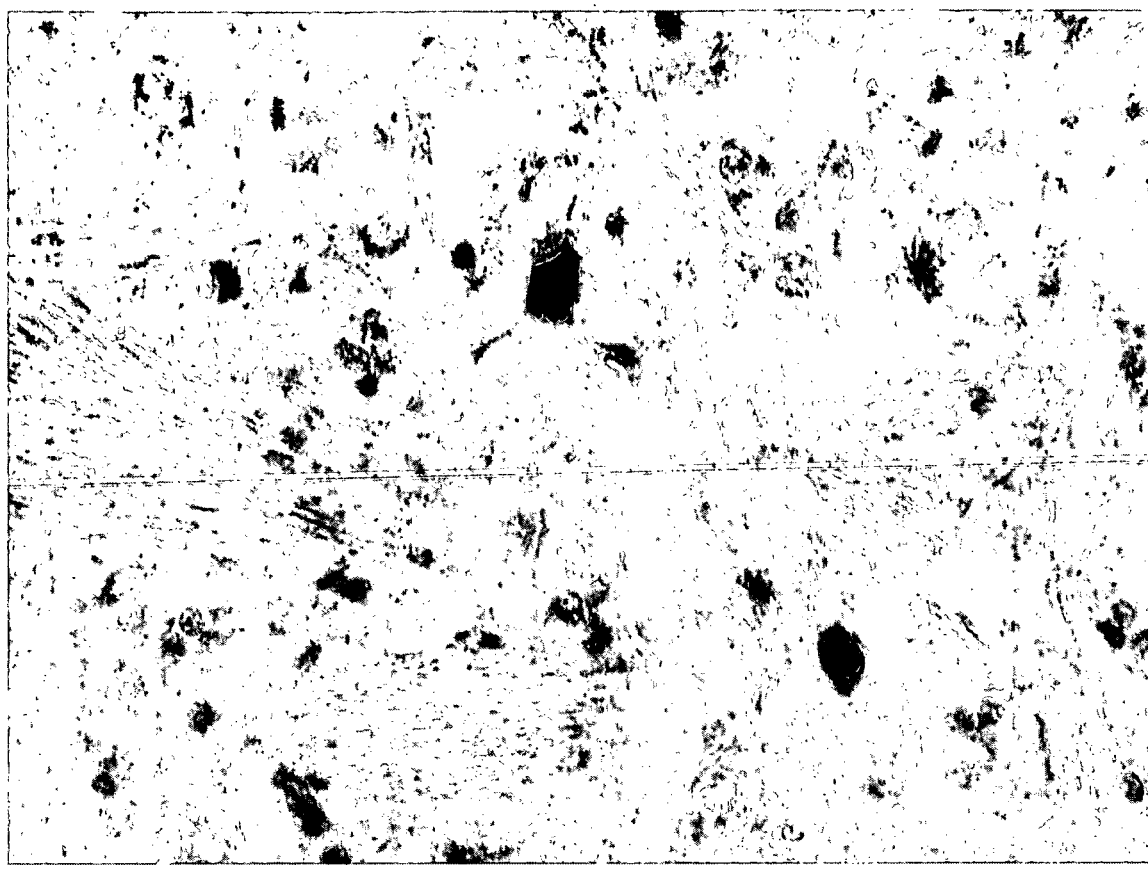
FIG. 18 is a photomicrograph showing an amber-brown human neuron with the branching extensions at the center of the picture and a glial cell at the right lower corner of the picture in the rat putamen. These cells migrated from the cerebral ventricle of the animal that showed a 70% improvement in its rotational behavior 4 months after the intraventricular injection of 500,000 undifferentiated brain progenitor cells. Anti-human mitochondrial antibodies. 40×

FIG. 18 is a photomicrograph showing an amber-brown human neuron with the branching extensions at the center of the picture and a glial cell at the right lower corner of the picture in the rat putamen. These cells migrated from the cerebral ventricle of the animal that showed a 70% improvement in its rotational behavior 4 months after the intraventricular injection of 500,000 undifferentiated neural progenitor cells. Anti-human mitochondrial antibodies. 40×

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A cell culture comprising:
   (a) a culture medium, wherein the calcium concentration of the medium is about 0.03 mM to 0.15 mM;
   (b) about 20-100 ng/ml epidermal growth factor (EGF);
   (c) about 10-50 ng/ml basic fibroblast growth factor (bFGF);
   (d) about 1-150 ng/ml transforming growth factor-alpha (TGFα);
   (e) mammalian neural progenitor cells (NPC) immunopositive for Oct4 and nestin, and wherein the cells continue to proliferate for at least 1 year in vitro.

2. The cell culture of claim 1, further comprising:
   (f) about 0.03 to about 0.09 mM calcium chloride, wherein the medium is brought to full volume in a calcium-free minimum essential medium and has a total calcium concentration of less than 0.1 mM.

3. The cell culture of claim 1, further comprising:
   (g) about 7-30 ng/ml leukemia inhibiting factor (LIF).

4. The cell culture of claim 2, wherein the total calcium concentration is about 0.05 mM.

5. The cell culture of claim 1, wherein the EGF is about 20 ng/ml.

6. The cell culture of claim 1, wherein the bFGF is about 10 ng/ml.

7. The cell culture of claim 1, wherein the TGFα is about 10 ng/ml.

8. The cell culture of claim 3, wherein the LIF is about 10 ng/ml.

9. The cell culture of claim 1 wherein the culture medium is serum-free.

10. The cell culture of claim 1, further comprising 2% B27 supplement.

11. The cell culture of claim 1, wherein the growth factors EGF, bFGF and TGFα, are recombinant growth factors.

12. The cell culture of claim 1 wherein the cells and the growth factors are human.

13. The cell culture of claim 1, further comprising about 0.11 mg/ml sodium pyruvate.

14. The cell culture of claim 1, wherein the cells have a doubling rate of less than 12 days.

15. The cell culture of claim 1, wherein the cells have a doubling rate of about 5 days.

16. The cell culture of claim 1, wherein the cells are obtained from fetal forebrain.

17. A method of propagating NPC that are immunopositive for nestin and Oct4, comprising culturing primary human fetal brain tissue in a culture medium, wherein the culture medium comprises:
    (a) 0.03 to 0.09 mM calcium;
    (b) about 20-100 ng/ml epidermal growth factor (EGF);
    (c) about 10-50 ng/ml fibroblast growth factor basic (bFGF); and
    (d) about 1-150 ng/ml transforming growth factor-alpha (TGFα),
    wherein the cells continue to proliferate for at least 1 year in vitro.

18. The method of claim 17, further comprising:
    (e) about 7-30 ng/ml leukemia inhibiting factor (LIF).

19. A method of transplanting human NPC to a mammalian host, comprising:
    (a) obtaining a cell culture of claim 1; and
    (b) transplanting the cell culture to the central nervous system (CNS) of the host, wherein the host has Parkinson's disease or epilepsy.

20. The method of claim 19, wherein glutamine (to a concentration 0.5 mM) and LIF (7-30 ng/ml) are added to the culture medium prior to the transplanting.

21. The method of claim 19, wherein the cell culture is transplanted to multiple sites within the host.

22. The method of claim 19, wherein the NPC are not genetically modified.

23. The method of claim 19, wherein the cell culture is transplanted to a ventricle of the central nervous system.

24. The method of claim 19, wherein the NPC are undifferentiated cells.

25. The method of claim 19, wherein the transplanting comprises intraparenchymal or intravenous administration.

26. The method of claim 19, wherein the NPC are undifferentiated at the time of transplanting.

27. A cell culture comprising human neural progenitor cells (NPC) that are immunopositive for nestin and Oct4 suspended in a medium, the medium consisting of:
    (a) a culture medium, wherein the calcium concentration of the medium is about 0.03 mM to about 0.09 mM;
    (b) about 20-100 ng/ml epidermal growth factor (EGF);
    (c) about 10-50 ng/ml basic fibroblast growth factor (bFGF);
    (d) about 1-150 ng/ml transforming growth factor-alpha (TGFα);
    (e) about 7-30 ng/ml leukemia inhibiting factor (LIF); and, optionally:
    (f) 2% B27 supplement;
    (g) about 0.11 mg/ml; sodium pyruvate.

28. A method of transplanting human NPC to a mammalian host, comprising:
    (a) obtaining a cell culture of undifferentiated NPC that are immunopositive for nestin and Oct4 suspended in a culture medium comprising:
        (i) about 20-100 ng/ml EGF;
        (ii) about 10-50 ng/ml bFGF;
        (iii) about 1-150 ng/ml TGFα;
        (iv) about 0.03 mM to 0.15 mM calcium; and
    (b) transplanting the undifferentiated cell culture to the central nervous system (CNS) of the host,
    wherein the host has Parkinson's disease or epilepsy.

29. A method of transplanting human NPC to a mammalian host, comprising:
    (a) obtaining a cell culture of NPC that are immunopositive for nestin and Oct4 suspended in a culture medium comprising:
        (i) about 20-100 ng/ml EGF;
        (ii) about 10-50 ng/ml bFGF;
        (iii) about 1-150 ng/ml TGFα; and
        (iv) about 0.03 mM to 0.15 mM calcium; and
    (b) transplanting the cell culture to the central nervous system (CNS) of the host, wherein the host has Parkinson's disease or epilepsy;
    wherein the NPC are not genetically modified.

* * * * *